(12) United States Patent
Utley et al.

(10) Patent No.: US 9,861,126 B2
(45) Date of Patent: Jan. 9, 2018

(54) SYSTEMS AND METHODS FOR QUANTIFICATION OF, AND PREDICTION OF SMOKING BEHAVIOR

(71) Applicant: Carrot, Inc., Redwood City, CA (US)

(72) Inventors: David S. Utley, Redwood City, CA (US); Allen Jameson, Sunnyvale, CA (US); Jennifer Marler, Oakland, CA (US)

(73) Assignee: Carrot, Inc., Redwood City, CA (US)

( * ) Notice: Subject to any disclaimer, the term of this patent is extended or adjusted under 35 U.S.C. 154(b) by 0 days.

(21) Appl. No.: 15/258,921

(22) Filed: Sep. 7, 2016

(65) Prior Publication Data

US 2017/0055573 A1 Mar. 2, 2017

Related U.S. Application Data

(63) Continuation of application No. 15/092,475, filed on Apr. 6, 2016.
(Continued)

(51) Int. Cl.
*A24F 47/00* (2006.01)
*A61B 5/097* (2006.01)
(Continued)

(52) U.S. Cl.
CPC ............ *A24F 47/00* (2013.01); *A61B 5/0022* (2013.01); *A61B 5/01* (2013.01); *A61B 5/021* (2013.01); *A61B 5/02405* (2013.01); *A61B 5/02438* (2013.01); *A61B 5/0533* (2013.01); *A61B 5/082* (2013.01); *A61B 5/083* (2013.01); *A61B 5/0816* (2013.01); *A61B 5/097* (2013.01); *A61B 5/14551* (2013.01); *A61B 5/4266* (2013.01); *A61B 5/681* (2013.01); *A61B 5/742* (2013.01); *G01N 33/497* (2013.01); *G08B 21/12* (2013.01);
(Continued)

(58) Field of Classification Search
CPC ...... G01N 30/06; G01N 30/32; G01N 1/2202; G01N 1/40; G01N 2030/025; A24F 47/00; A61B 5/082; A61B 5/097; G08B 21/12; H04Q 9/00; H04Q 2209/40
See application file for complete search history.

(56) References Cited

U.S. PATENT DOCUMENTS 3,953,566 A 4/1976 Gore
4,220,142 A 9/1980 Rosen et al.
(Continued)

FOREIGN PATENT DOCUMENTS

WO WO 1994/000831 1/1994
WO WO 2005/117621 12/2005
WO WO 2006/118654 11/2006

OTHER PUBLICATIONS

McMillan, A.S. et al., "Reflex inhibition in single motor units of the human lateral ptergoid muscle," *Experimental Brain Research*, 76: 97-102, 1989, Department of Oral Biology, University of British Columbia.
(Continued)

*Primary Examiner* — Orlando Bousono
(74) *Attorney, Agent, or Firm* — Levine Bagade Han LLP

(57) ABSTRACT

Systems and methods for monitoring of biometric and contextual variables to assist in screening for, quantification of, and prediction of smoking behavior, and for assisting in smoking cessation are described.

27 Claims, 21 Drawing Sheets

Related U.S. Application Data

(60) Provisional application No. 62/143,924, filed on Apr. 7, 2015.

(51) Int. Cl.

| | | |
|---|---|---|
| *G01N 33/497* | (2006.01) | |
| *A61B 5/00* | (2006.01) | |
| *A61B 5/01* | (2006.01) | |
| *A61B 5/021* | (2006.01) | |
| *A61B 5/024* | (2006.01) | |
| *A61B 5/053* | (2006.01) | |
| *A61B 5/08* | (2006.01) | |
| *A61B 5/1455* | (2006.01) | |
| *A61B 5/083* | (2006.01) | |
| *G08B 21/12* | (2006.01) | |
| *H04Q 9/00* | (2006.01) | |
| *H04W 84/18* | (2009.01) | |

(52) U.S. Cl.
CPC .......... *H04Q 9/00* (2013.01); *A61B 2562/046* (2013.01); *H04Q 2209/40* (2013.01); *H04W 84/18* (2013.01)

(56) References Cited

U.S. PATENT DOCUMENTS

| | | | |
|---|---|---|---|
| 4,246,913 A | 1/1981 | Ogden et al. | |
| 4,277,452 A | 7/1981 | Kanehori et al. | |
| 4,585,417 A | 4/1986 | Sozio et al. | |
| 4,609,349 A | 9/1986 | Cain | |
| 4,615,681 A | 10/1986 | Schwarz | |
| 4,629,424 A | 12/1986 | Lauks et al. | |
| 4,853,854 A | 8/1989 | Behar et al. | |
| 4,896,143 A * | 1/1990 | Dolnick | G01N 27/124 |
| | | | 340/634 |
| 4,904,520 A | 2/1990 | Dumas et al. | |
| 4,971,558 A | 11/1990 | Jacobi | |
| 4,992,049 A | 2/1991 | Weissman | |
| 4,996,161 A | 2/1991 | Conners et al. | |
| 5,021,457 A | 6/1991 | Akin et al. | |
| 5,035,860 A | 7/1991 | Kleingeld et al. | |
| 5,063,164 A | 11/1991 | Goldstein | |
| 5,188,109 A | 2/1993 | Saito | |
| 5,284,163 A | 2/1994 | Knudsen et al. | |
| 5,361,771 A * | 11/1994 | Craine | A61B 5/0813 |
| | | | 600/473 |
| 5,565,152 A | 10/1996 | Od et al. | |
| 5,618,493 A | 4/1997 | Goldstein et al. | |
| 5,764,150 A * | 6/1998 | Fleury | G01N 33/004 |
| | | | 340/632 |
| 5,778,897 A | 7/1998 | Nordlicht | |
| 5,829,971 A | 11/1998 | Razdolsky et al. | |
| 5,841,021 A | 11/1998 | De et al. | |
| 5,908,301 A | 6/1999 | Lutz | |
| 6,039,688 A | 3/2000 | Douglas et al. | |
| 6,164,278 A | 12/2000 | Nissani | |
| 6,340,588 B1 | 1/2002 | Nova et al. | |
| 6,397,093 B1 | 5/2002 | Aldrich | |
| 6,544,199 B1 | 4/2003 | Morris | |
| 6,602,892 B1 | 8/2003 | Sachs | |
| 6,613,001 B1 | 9/2003 | Dworkin | |
| 6,730,494 B1 | 5/2004 | Toranto et al. | |
| 6,748,792 B1 | 6/2004 | Freund et al. | |
| 6,858,182 B1 | 2/2005 | Ito et al. | |
| 7,054,679 B2 | 5/2006 | Hirsh | |
| 7,163,511 B2 | 1/2007 | Conn et al. | |
| 7,408,640 B2 | 8/2008 | Cullum et al. | |
| 7,421,882 B2 | 9/2008 | Leddy et al. | |
| 7,451,852 B2 | 11/2008 | Stewart et al. | |
| 7,525,093 B2 | 4/2009 | Stenberg | |
| 7,610,919 B2 | 11/2009 | Utley et al. | |
| 7,661,955 B2 | 2/2010 | Da | |
| 7,716,383 B2 | 5/2010 | Lei et al. | |
| 7,720,516 B2 | 5/2010 | Chin et al. | |
| 7,797,982 B2 | 9/2010 | Burke et al. | |
| 7,899,518 B2 | 3/2011 | Trepagnier et al. | |
| 8,130,105 B2 | 3/2012 | Al-Ali et al. | |
| 8,160,279 B2 | 4/2012 | Abolfathi | |
| 8,190,223 B2 | 5/2012 | Al-Ali et al. | |
| 8,224,411 B2 | 7/2012 | Al-Ali et al. | |
| 8,224,667 B1 | 7/2012 | Miller et al. | |
| 8,235,921 B2 | 8/2012 | Rousso et al. | |
| 8,249,311 B2 | 8/2012 | Endo et al. | |
| 8,560,032 B2 | 10/2013 | Al-Ali et al. | |
| 2001/0027384 A1 | 10/2001 | Schulze et al. | |
| 2001/0027794 A1 | 10/2001 | Brue | |
| 2002/0061495 A1 | 5/2002 | Mault | |
| 2002/0072959 A1 | 6/2002 | Clendonon | |
| 2002/0146346 A1 | 10/2002 | Konecke | |
| 2002/0177232 A1 | 11/2002 | Melker et al. | |
| 2003/0003113 A1 | 1/2003 | Lewandowski | |
| 2003/0004403 A1 | 1/2003 | Drinan et al. | |
| 2003/0004426 A1 * | 1/2003 | Melker | G01N 29/022 |
| | | | 600/532 |
| 2003/0015019 A1 * | 1/2003 | O'Brien | G01N 1/2202 |
| | | | 73/23.2 |
| 2003/0149372 A1 * | 8/2003 | Smith | A61B 5/083 |
| | | | 600/532 |
| 2003/0211007 A1 | 11/2003 | Maus et al. | |
| 2004/0006113 A1 | 1/2004 | Sachs | |
| 2004/0031498 A1 | 2/2004 | Brue | |
| 2004/0035183 A1 * | 2/2004 | O'Brien | G01N 1/2202 |
| | | | 73/23.27 |
| 2004/0158194 A1 | 8/2004 | Wolff et al. | |
| 2004/0239510 A1 | 12/2004 | Karsten | |
| 2005/0053523 A1 | 3/2005 | Brooke | |
| 2005/0081601 A1 | 4/2005 | Lawson | |
| 2005/0112148 A1 | 5/2005 | Dmitruk | |
| 2005/0141346 A1 | 6/2005 | Rawls et al. | |
| 2005/0163293 A1 | 7/2005 | Hawthorne et al. | |
| 2005/0171816 A1 | 8/2005 | Meinert et al. | |
| 2005/0177056 A1 | 8/2005 | Giron et al. | |
| 2005/0177615 A1 | 8/2005 | Hawthorne et al. | |
| 2005/0263160 A1 | 12/2005 | Utley et al. | |
| 2006/0144126 A1 * | 7/2006 | O'Brien | G01N 1/2202 |
| | | | 73/23.42 |
| 2006/0167723 A1 | 7/2006 | Berg | |
| 2006/0193749 A1 | 8/2006 | Ghazarian et al. | |
| 2006/0220881 A1 | 10/2006 | Al et al. | |
| 2006/0226992 A1 | 10/2006 | Al et al. | |
| 2006/0229914 A1 | 10/2006 | Armstrong | |
| 2006/0237253 A1 | 10/2006 | Mobley et al. | |
| 2006/0238358 A1 | 10/2006 | Al et al. | |
| 2007/0005988 A1 | 1/2007 | Zhang et al. | |
| 2007/0164220 A1 * | 7/2007 | Luk | G01N 21/33 |
| | | | 250/338.5 |
| 2007/0168501 A1 | 7/2007 | Cobb et al. | |
| 2007/0209669 A1 | 9/2007 | Derchak | |
| 2007/0271997 A1 * | 11/2007 | O'Brien | G01N 1/2202 |
| | | | 73/23.37 |
| 2007/0277823 A1 | 12/2007 | Al Ali et al. | |
| 2007/0277836 A1 | 12/2007 | Longley | |
| 2007/0282226 A1 | 12/2007 | Longley | |
| 2007/0282930 A1 | 12/2007 | Doss et al. | |
| 2008/0078232 A1 | 4/2008 | Burke et al. | |
| 2008/0146890 A1 | 6/2008 | LeBoeuf et al. | |
| 2008/0162352 A1 | 7/2008 | Gizewski | |
| 2008/0199838 A1 | 8/2008 | Flanagan | |
| 2008/0221418 A1 | 9/2008 | Al-Ali et al. | |
| 2009/0069642 A1 | 3/2009 | Gao et al. | |
| 2009/0164141 A1 | 6/2009 | Lee | |
| 2009/0191523 A2 | 7/2009 | Flanagan | |
| 2009/0216132 A1 | 8/2009 | Orbach | |
| 2009/0253220 A1 | 10/2009 | Banerjee | |
| 2009/0293589 A1 | 12/2009 | Freund et al. | |
| 2009/0325639 A1 | 12/2009 | Koehn | |
| 2010/0009324 A1 | 1/2010 | Owens et al. | |
| 2010/0010321 A1 | 1/2010 | Foster | |
| 2010/0010325 A1 | 1/2010 | Ridder et al. | |
| 2010/0010433 A1 | 1/2010 | Krogh et al. | |
| 2010/0012417 A1 | 1/2010 | Walter et al. | |

(56) References Cited

U.S. PATENT DOCUMENTS

| | | | |
|---|---|---|---|
| 2010/0081955 A1* | 4/2010 | Wood, Jr. | A61B 5/097 600/532 |
| 2010/0116021 A1* | 5/2010 | O'Brien | G01N 1/2202 73/23.37 |
| 2010/0204600 A1 | 8/2010 | Crucilla | |
| 2010/0209897 A1 | 8/2010 | Utley et al. | |
| 2010/0298683 A1 | 11/2010 | Cabrera et al. | |
| 2011/0035158 A1* | 2/2011 | Banos | A61B 5/08 702/19 |
| 2011/0079073 A1 | 4/2011 | Keays | |
| 2011/0153223 A1* | 6/2011 | Gentala | G01N 21/3504 702/24 |
| 2011/0247638 A1 | 10/2011 | Ayala | |
| 2011/0263947 A1* | 10/2011 | Utley | A61B 5/082 600/300 |
| 2011/0265552 A1* | 11/2011 | Stedman | G01M 15/102 73/23.31 |
| 2011/0270052 A1 | 11/2011 | Jensen et al. | |
| 2011/0270053 A1 | 11/2011 | Utley et al. | |
| 2011/0295140 A1* | 12/2011 | Zaidi | A61B 5/0075 600/532 |
| 2012/0022890 A1 | 1/2012 | Williams et al. | |
| 2012/0068848 A1 | 3/2012 | Campbell et al. | |
| 2012/0115115 A1 | 5/2012 | Rapoza | |
| 2012/0130584 A1* | 5/2012 | Stedman | G01M 15/108 701/31.5 |
| 2012/0161970 A1 | 6/2012 | Al-Ali et al. | |
| 2012/0190955 A1 | 7/2012 | Rao et al. | |
| 2012/0191052 A1 | 7/2012 | Rao | |
| 2012/0232359 A1 | 9/2012 | Al-Ali et al. | |
| 2012/0238834 A1 | 9/2012 | Hornick | |
| 2012/0294876 A1* | 11/2012 | Zimmerman | A61B 5/082 424/184.1 |
| 2013/0233052 A1* | 9/2013 | Stedman | G01M 15/108 73/23.31 |
| 2013/0253849 A1* | 9/2013 | Gentala | G01N 21/3504 702/24 |
| 2013/0316926 A1 | 11/2013 | Caffrey | |
| 2014/0033796 A1* | 2/2014 | Stedman | G01M 15/102 73/23.31 |
| 2014/0051043 A1 | 2/2014 | Mosby | |
| 2014/0228699 A1 | 8/2014 | Causevic et al. | |
| 2014/0358018 A1* | 12/2014 | Neagle, III | G06F 19/322 600/532 |
| 2015/0024355 A1* | 1/2015 | Ghofrani | F23Q 2/325 434/236 |
| 2015/0025407 A1* | 1/2015 | Eichler | A61B 5/087 600/532 |
| 2015/0032019 A1* | 1/2015 | Acker | A61B 5/082 600/532 |
| 2015/0064672 A1 | 3/2015 | Bars | |
| 2015/0065825 A1 | 3/2015 | Utley et al. | |
| 2015/0201865 A1* | 7/2015 | Forzani | A61B 5/082 600/532 |
| 2016/0029693 A1 | 2/2016 | Klein et al. | |

OTHER PUBLICATIONS

Navy Cyanide Test Kit (NACTEK), http://www.nrl.navy.mil/research/nrl- review/2004/chemical-biochemical-researchl deschamps/, accessed Oct. 26, 2010.

Sung, M. et al., "Wearable feedback systems for rehabilitation," *Journal of NeuroEngineering and Rehabilitation*, 2:17, pp. 1-12, Jun. 2005.

Wu, W.H. et al., "MEDIC: Medical embedded device for individualized care," Artificial Intelligence in Medicine,42(2):137-152, Feb. 2008.

Varshney, U. "Wireless Health Monitoring: Requirements and Examples," Pervasive Healthcare Computing: EMR/EHR, Chapter 5, pp. 89-118, Apr. 21, 2009, Spring Science+Business LLC.

* cited by examiner

```
600
    <PATIENT DATA>
602    <NAME> JOE SMITH </NAME>
604    <AGE> 52 </AGE>
606    <CURVE DATA>
608        <CURVE IDENTIFIER> 27 </CURVE IDENTIFIER>
610        <DAY> 01 </DAY>
612        <TIME> 12:28 </TIME>
612        <LOCATION> WORK </LOCATION>
612        <CO LEVEL> 5% </CO LEVEL>
614        <O2 LEVEL> 95% </O2 LEVEL>
614        ...
616        <TRIGGER> LUNCH </TRIGGER>
           ...
618        <CURVE IDENTIFIER> 28 </CURVE IDENTIFIER>
           ...
       </CURVE DATA>
       ...
    </PATIENT DATA>
```

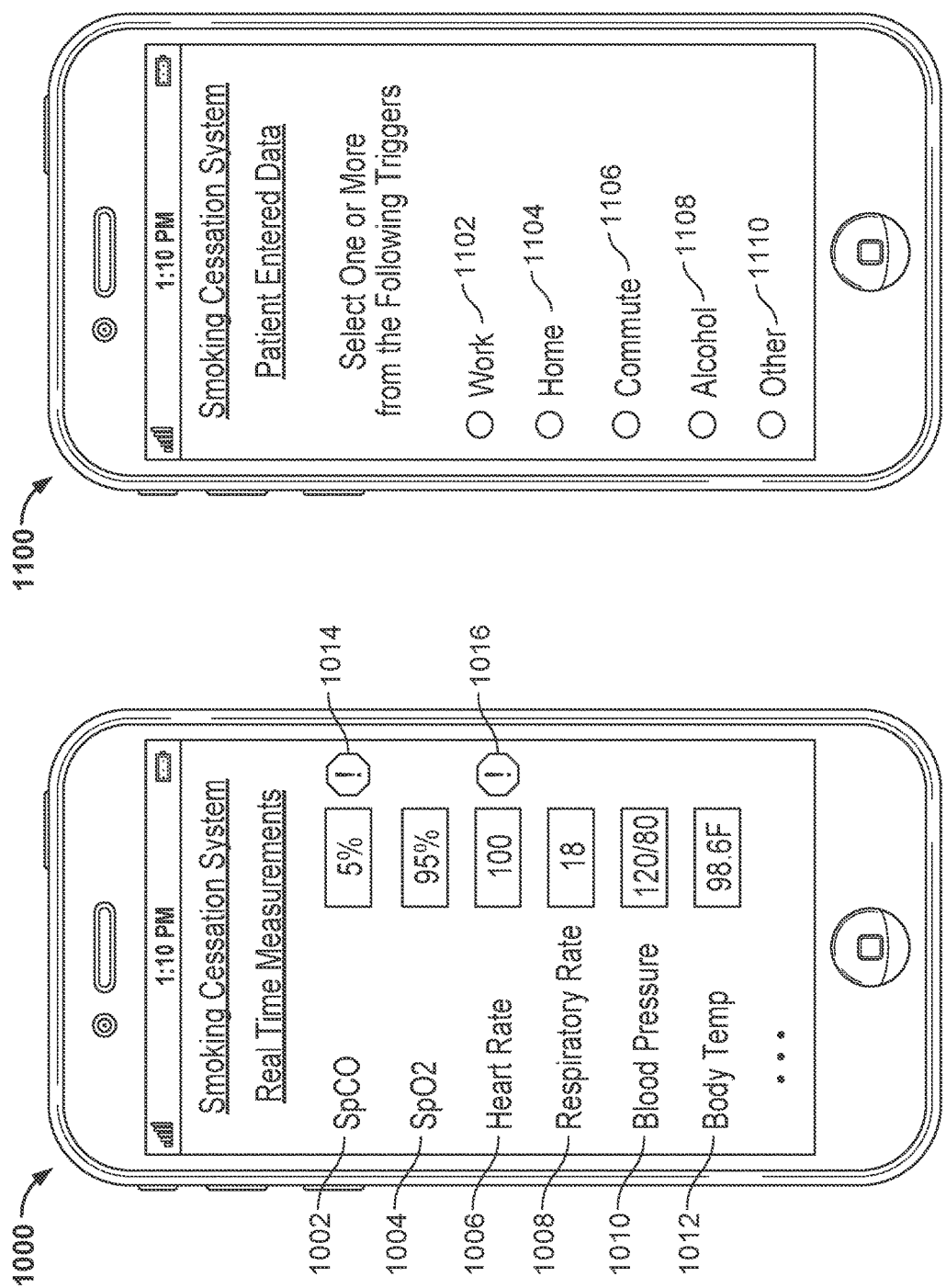

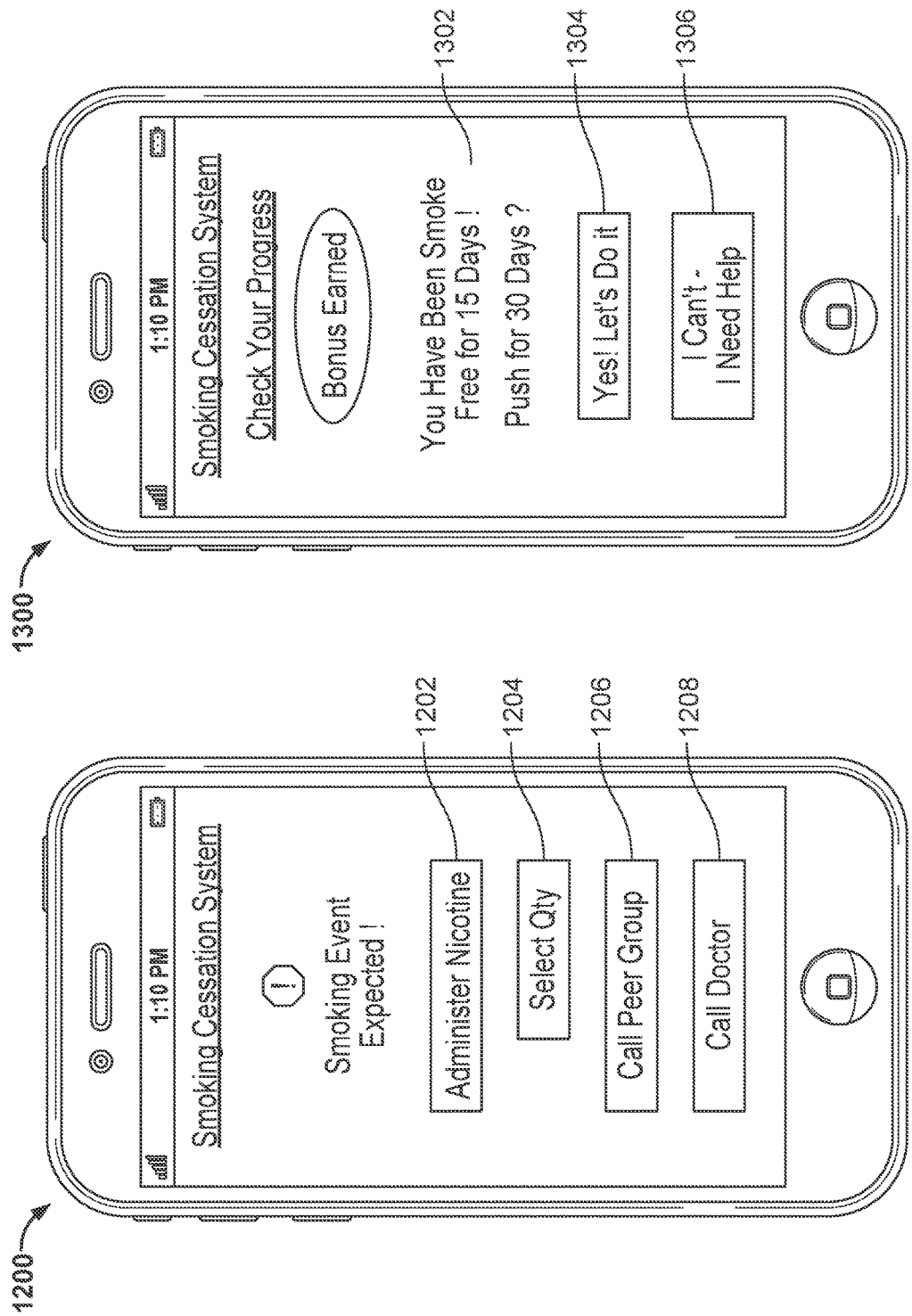

SYSTEMS AND METHODS FOR QUANTIFICATION OF, AND PREDICTION OF SMOKING BEHAVIOR

RELATED APPLICATION

This is a continuation of U.S. patent application Ser. No. 15/092,475 filed Apr. 6, 2016, which is a non-provisional application of U.S. Provisional Application No. 62/143,924 filed on Apr. 7, 2015, the entirety of both of which are incorporated by reference.

FIELD OF THE INVENTION

The present disclosure relates to systems and methods for monitoring of biometric and contextual variables to assist in screening for smoking cessation. The systems and methods may non-invasively detect smoking behavior for a patient. The systems and methods may quantify and/or predict smoking behavior of the patient. The systems and methods may assist in smoking cessation. In some embodiments, the systems and methods provide for screening a general population during medical and dental visits and other suitable health related appointments. In some embodiments, the systems and methods provide for initiating and setting up a quit program for a patient who smokes. In some embodiments, the systems and methods provide for a follow up program after the patient successfully quits smoking.

BACKGROUND

The health problems associated with tobacco smoking are well known. Cigarette smoke contains nicotine as well as many other chemical compounds and additives. Tobacco smoke exposes an individual to carbon monoxide as well as these other compounds, many of which are carcinogenic and toxic to the smoker and those around the smoker. The presence and level of carbon monoxide in the exhaled breath of the smoker can provide a marker for identifying the overall smoking behavior of that individual as well as provide a marker for their overall exposure to the other toxic compounds.

Because of the health risks and problems associated with smoking, in addition to the effects of smoke on exposed non-smokers, many programs exist to assist an individual in cessation of smoking or at least reduce the amount of smoking on a daily basis.

Smoking cessation programs and products typically attempt to reduce the patient's smoking without fully understanding the smoking behavior that can vary between patients. In addition, it may be difficult to understand a patient's smoking behavior given that self-reporting of smoking behavior relies on strict compliance with reporting smoking activities. And in many cases, individuals may not strictly comply with reporting such activities due to shame, carelessness, and/or human error associated with tracking and assessing cigarette smoking.

There remains a need to address smoking in individuals by first understanding the individual's smoking behavior and then, based on this understanding, engage the individual with effective means for reducing and ultimately stopping smoking.

SUMMARY OF THE INVENTION

The system and methods described herein allow for a multi-phased approach to engaging individuals that smoke and quantifying their smoking behavior to better assist the individual to eventually achieve the goal of smoking cessation. The methods and systems described herein allow for improved measuring and quantifying of a smoker's behavior before that individual is even given the difficult task of attempting to quit smoking. For example, the systems and methods described herein are useful to identify a population of smokers from within a larger population using objective criteria. Once the individual smoker is identified, the same methods and systems allow for a learn and explore phase where the individual's specific smoking behavior can be tracked and quantified. The methods and systems also allow for the individual's behavioral data to be tracked to identify potential triggers to smoking or simply to educate the individual on the extent of their smoking. The methods and systems also allow for a more active monitoring of the individual that has decided to engage in a "quit" program, where such monitoring allows the individual to self-monitor as well as monitoring by peers, coaches, or counselors. Lastly, the methods and systems disclosed herein can be used to monitor the individuals who successfully quit smoking to ensure that smoking behavior does not re-occur.

Systems and methods for assessment of a smoking behavior of an individual are described herein. The system can permit quantifying the individual's smoking behavior by measuring biometric data and assessing for factors attributable to cigarette smoke as well as assessing behavioral data associated with smoking or with the individual's ordinary activity.

The systems and methods non-invasively can detect and quantify smoking behavior for a patient based on measuring one or more of the patient's biometric data such as CO level or exhaled CO level. However other biometric data can also be used. Such data includes carboxyhemoglobin (SpCO), oxyhemoglobin (SpO2), heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. Such measurements or data collection can use a portable measuring unit or a fixed measuring unit, either of which communicates with one or more electronic devices for performing the quantification analysis. Alternatively, the analysis can be performed in the portable/fixed unit. For example, the portable unit can be coupled to a keychain, to the individual's cigarette lighter, cell phone, or other item that will be with the individual on a regular basis. Alternatively, the portable unit can be a stand-alone unit or can be worn by the individual.

In one variation, the methods described herein permit quantifying an individual's smoking behavior by obtaining a plurality of samples of exhaled air from the individual over a period of time and recording a collection time associated with each sample of exhaled air; measuring an amount of exhaled carbon monoxide for each of the samples of exhaled air; compiling a dataset comprising the amount of exhaled carbon monoxide and the collection time for each sample of exhaled air; quantifying an exposure of exhaled carbon monoxide over an interval of time within the period of time and assigning an exhaled carbon monoxide load to the interval of time using the dataset; and displaying the exhaled carbon monoxide load. Displaying the quantified result can occur at one or more locations to provide feedback to the individual, a caregiver, or any other individual having a stake in understanding and/or reducing the individual's smoking behavior.

In an additional variation, obtaining the plurality of samples of exhaled air from the individual over the period of time and recording the collection time of each sample of exhaled air comprises sequentially obtaining the plurality of sample of exhaled air.

Quantifying the exposure of exhaled carbon monoxide can comprise correlating a function of exhaled carbon monoxide versus time over the period of time using the dataset. Alternatively, the quantification can comprise a mathematical product of the CO level and time over the interval of time. Such quantification allows for an improved observation of the smoking behavior since it allows observation of the total exposure of the body to CO over a given interval of time.

In an additional variation, the method further comprises obtaining an area of exhaled carbon monoxide and time under a curve defined by the function over the interval of time.

The method and system can further include comprising generating a signal, e.g., using a portable device positioned with the individual, to remind the individual to provide at least one sample of exhaled air. In additional variations, the method can include alerting the individual on a repeating basis to provide the sample of exhaled air over the period of time.

The method above can also include receiving an input data from the individual and recording a time of the input. Such data can include behavioral data such as a count of a portion of a cigarette smoked by the individual. Alternatively, the data can include information on location (via a GPS unit), diet, activity (e.g., driving, watching TV, dining, working, socializing, etc.).

The method can include visually displaying any of the input data. Including a summation of the count of portion of the cigarettes smoked by the individual. Such data can also allow the display of calculated information. For example, a cigarette count can be used to determine an individual's nicotine exposure from cigarettes when a direct biological measurement might also erroneously measure nicotine from a nicotine patch or nicotine gum. In addition, the cigarette data can be used to estimate a cost associated with the number of cigarettes smoked by the individual and displaying such a cigarette cost.

The method can further comprise providing the visual display of the exhaled carbon monoxide load in association with a visual display interval of time within the period of time. Additionally, the method can include providing a visual display of a count of a number of the plurality of samples of exhaled air.

The method can also include determining a series of exhaled carbon monoxide loads for a series of intervals of time within the period of time. These values can be displayed in addition to the information discussed herein.

The method can further include transmitting the amount of exhaled carbon monoxide and the collection time associated with each sample of exhaled air from the portable sensor to an electronic device.

Another variation of quantifying an individual's smoking behavior can include obtaining a plurality of samples of carbon monoxide from the individual over a period of time and recording a collection time associated with each sample of carbon monoxide; compiling a dataset comprising the amount of carbon monoxide and the collection time for each sample of carbon monoxide; quantifying an exposure of carbon monoxide over an interval of time within the period of time and assigning a carbon monoxide load to the interval of time using the dataset; and displaying the carbon monoxide load. In such a case, the amount of carbon monoxide is determined from any type of measurement that identifies carbon monoxide levels in the body.

The method can further comprise obtaining the plurality of samples of carbon monoxide comprises obtaining a plurality of samples of exhaled air from the individual over time and measuring an amount of exhaled carbon monoxide for each of the samples of exhaled air and where recording the collection time associated with each sample of carbon monoxide comprises recording the collection time associated with each sample of exhaled air.

The present disclosure also includes a device for obtaining data to quantify an individual's smoking behavior. Where such a device can assist or perform the functions described herein.

In one example, the device includes a portable breathing unit configured to receive a plurality of samples of exhaled air from the individual over a period of time and configured to recording a collection time associated with each sample of exhaled air; a sensor located within the unit and configured to measure an amount of exhaled carbon monoxide for each of the samples of exhaled air; at least one an input switch configured to record input data from the individual; a storage unit configured to store at least the amount of exhaled carbon monoxide and the collection time; a transmitter configured to transmit the amount of exhaled carbon monoxide, the collection time, and input data to an external electronic device; and an alarm unit configured to provide an alarm to the user for submitting the plurality of samples of exhaled air.

The methods described herein can also include methods for preparing a program to assist in cessation of smoking for a patient who smokes. For example, the method can include measuring at least one biological indicator determinative of whether the patient smoked; capturing a plurality of patient data, where the patient data comprises information correlated in time to when the patient smoked; combining at least one of the plurality of patient data and at least one biological indicator to determine a smoking behavior model of the patient during a first testing period; assessing the smoking behavior model to assess a degree of intervention required for a quit program; and providing a summary report of the smoking behavior model and the degree of intervention.

In another variation, the present disclosure includes a system for deterring a patient from smoking. For instance, the system can include a sensor for measuring at least one biological indicator determinative of whether the patient smoked; a data collecting device configured to capture a plurality of patient data, where the patient data comprises information correlated in time to when the patient smoked; a processor in communication with the sensor and data collecting device, the processor configured to compile the plurality of patient data and at least one biological indicator to determine a smoking behavior model of the patient over a first testing period; the processor configured to generate at least one perturbation signal before a second testing period, and where the processor analyzes at least one of the patient data captured over the second testing period to determine a tested smoking behavior; and where the processor compares the tested smoking behavior to the model smoking behavior to determine whether the patient was deterred from smoking.

The present disclosure also includes methods for deterring a patient from smoking. For example, such a method can include measuring at least one biological indicator determinative of whether the patient smoked; collecting a plurality of patient data, where the patient data comprises information correlated in time to when the patient smoked; compiling the plurality of patient data with the at least one biological indicator to determine a smoking behavior model of the patient; generating at least one perturbation signal before a second testing period, where the at least one perturbation signal affects the patient; analyzing at least one of the patient data captured over the second testing period to determine a tested smoking behavior; and comparing the tested smoking behavior to the model smoking behavior to determine a change from the smoking behavior model to determine whether the patient was deterred from smoking.

In another variation, a system for deterring a patient from smoking can include a database containing a smoking behavior model of the patient, where the smoking behavior model comprises a plurality of historical patient data correlated in time to when the patient smoked; a sensor for measuring at least one biological indicator determinative of whether the patient smoked; a processor configured to determine an expected smoking event upon analyzing the smoking behavior model and upon determining the expected smoking event the processor generates at least one perturbation signal prior to a testing period; the processor configured to review the at least one biological indicator during the testing period to determine whether the patient was deterred from smoking during the testing period; and where the processor updates the database containing the smoking behavior model after determining whether or not the patient was deterred from smoking during the testing period.

Another variation of the method for deterring smoking can include accessing a database containing a smoking behavior model of the patient, where the smoking behavior model comprises a plurality of historical patient data correlated in time to when the patient smoked; estimating an expected smoking event upon analyzing the smoking behavior model; generating at least one perturbation signal prior to a testing period upon determining the expected smoking event the processor; measuring at least one biological indicator determinative of whether the patient smoked during the testing period; reviewing the at least one biological indicator during the testing period to determine whether the patient was deterred from smoking during the testing period; and updating the database containing the smoking behavior model after determining whether or not the patient was deterred from smoking during the testing period.

The above is a brief description of some the methods and systems to quantify a smoking behavior as well as programs for effective smoking cessation. Other features, advantages, and embodiments of the invention will be apparent to those skilled in the art from the following description and accompanying drawings, wherein, for purposes of illustration only, specific forms of the invention are set forth in detail. Variations of the access device and procedures described herein include combinations of features of the various embodiments or combination of the embodiments themselves wherever possible.

Although the present disclosure discusses cigarettes in the various examples, the methods, systems and improvements disclosed herein can be applied to any type of tobacco smoke or other inhaled type of smoke. In such cases, the disclosure contemplate the replacement of "cigarette" with the appropriate type of tobacco or smoke generating product (including, but not limited to, cigars, pipes, etc.)

BRIEF DESCRIPTION OF THE DRAWINGS

FIG. 10 depicts an illustrative smart phone app screen showing measurements such as SpCO, SpO2, heart rate, respiratory rate, blood pressure, and body temperature in accordance with some embodiments of the disclosure;

FIG. 11 depicts an illustrative smart phone app screen for receiving patient entered data in accordance with some embodiments of the disclosure;

FIG. 12 depicts an illustrative smart phone app screen implementing a smoking prevention protocol in accordance with some embodiments of the disclosure;

FIG. 13 depicts an illustrative smart phone app screen for presenting the quit process as a game for the patient in accordance with some embodiments of the disclosure;

DETAILED DESCRIPTION THE INVENTION

Figure 1:
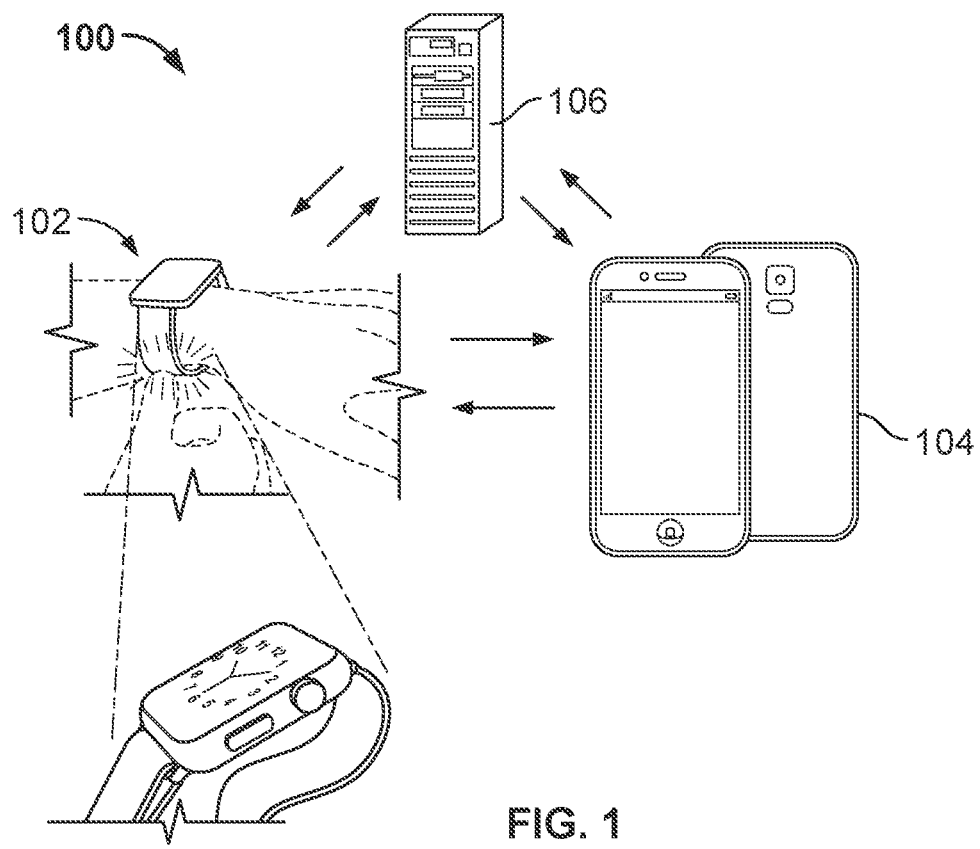
FIG. 1 depicts an illustrative system including a wearable device, a mobile device, and a remote server in communication with the wearable device and the mobile device in accordance with some embodiments of the disclosure.

Systems and methods for smoking cessation with interactive screening are described. The systems and methods non-invasively detect and quantify smoking behavior for a patient based on measuring one or more of the patient's carbon monoxide levels, exhaled carbon monoxide levels (eCO), carboxyhemoglobin (SpCO), oxyhemoglobin (SpO2), heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. It is noted that SpCO and eCO are two ways to measure of the CO levels in the patient's blood.

In some embodiments, the systems and methods described herein provide for screening a general population during medical and dental visits and other suitable health related appointments. A wearable device may be applied to patients during, e.g., their annual visits, to detect recent smoking behavior and, if positive, refer the smokers for further testing and ultimately to a smoking cessation program. In some embodiments, the wearable device is applied as a one time on-the-spot measurement. In some embodiments, the patient is provided with a wearable device to wear as an outpatient for a period of time, e.g., one day, one week, or another suitable period of time. Longer wear times may provide more sensitivity in detection of smoking behavior and more accuracy in quantifying the variables related to smoking behavior.

When wearing the wearable device for a suitable period of time, e.g., five days, a number of parameters may be measured real-time or near real time. These parameters may include, but are not limited to, CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. Data from the wearable device may be sent to a smart phone or a cloud server or another suitable device, either in real time, near real time, at the end of each day, or according to another suitable time interval. The wearable device or the smart phone may measure parameters, including but not limited to, movement, location, time of day, patient entered data, and other suitable parameters. The patient entered data may include stressors, life events, location, daily events, administrations of nicotine patches or other nicotine formulas, administrations of other drugs for smoking cessation, and other suitable patient entered data. For example, some of the patient entered data may include information regarding phone calls, athletics, work, sport, stress, sex, drinking, smoking, and other suitable patient entered data. The received data may be compiled, analyzed for trends, and correlated either real time or after the period of time is complete.

From the parameters measured above, information regarding smoking may be derived via a processor located in the wearable device, the smart phone, the cloud server, or another suitable device. For example, the processor may analyze the information to determine CO, eCO, SpCO trends, averages, peaks, changes, specific curve signatures, slopes of change and other types of changes, and determine associations with other biometric and contextual variable trends during day, and how those variables change before, during and after smoking. The processor may analyze the CO, eCO, SpCO trends to determine parameters such as total number of cigarettes smoked, average number of cigarettes smoked per day, maximum number of cigarettes smoked per day, intensity of each cigarette smoked, quantity of each cigarette smoked, time to smoke each cigarette, time of day, day of week, associated stressors, geography, location, and movement. For example, the total number of peaks in a given day may indicate the number of cigarettes smoked, while the shape and size and other characteristics of each peak may indicate the intensity and amount of each cigarette smoked. The processor may analyze heart rate and/or pulse rate data to determine correlations between trends, averages, and peaks and patient smoking behavior. For example, the processor may correlate changes in heart rate, such as tachycardia or heart rate variability, that occurs before or during a smoking event that can predict when a patient will smoke. This information may be used to preempt a smoking event during a quit program. For example, if a smoking event is predicted to occur within the next 10 minutes, the patient may be notified to deliver a dose of nicotine by any of a number of mechanisms such as delivery via a transdermal patch or a transdermal transfer from a reservoir of nicotine stored in the wearable device.

In some embodiments, the systems and methods described herein provide for evaluating smoking behavior of a patient in two testing periods. During a first testing period, the patient behaves as they normally would. The processor located in the wearable device, the smart phone, the cloud server, or another suitable device receives patient data relating to the patient's smoking behavior. There is very little to no engagement of the patient as the purpose of the testing period is to observe the patient's smoking patterns. Before the second testing period, the processor determines a model of how the patient smokes.

During a second testing period, the processor applies a series of perturbations to the model to see if the smoking behavior changes. The perturbations may be applied to the model using a machine learning process. The machine learning process delivers perturbations, tests the results, and adjusts the perturbation accordingly. The processor determines what works best to achieve an identified behavior change by trying options via the machine learning process.

There may be several types of perturbations, each with several dimensions. For example, the perturbation may be whether sending a text message before or during a smoking event causes the smoking event to be averted or shortened. Dimensions within the perturbation may be different senders, different timing, and/or different content for the text messages. In another example, the perturbation may be whether a phone call at certain times of the day or before or during a smoking event causes the smoking event to be averted or shortened. Dimensions within the perturbation may be different callers, different timing, and/or different content for the phone calls. In yet another example, the perturbation may be whether alerting the patient to review their smoking behavior at several points in the day averts smoking for a period of time thereafter. Dimensions may include determining whether and when that aversion extinguishes. In other examples, the perturbations may be rewards, team play, or other suitable triggers to avert or shorten the patient's smoking events.

In some embodiments, the systems and methods described herein provide for initiating and setting up a quit program for a patient. After the patient has completed a five-day evaluation while wearing the wearable device, the full dataset is compiled and analyzed by the system and delivered to the patient or a doctor for the quit program. For example, a sample report may indicate that, from October 1 to October 6, Mr. Jones smoked a total of 175 cigarettes with an average number of 35 cigarettes smoked per day, and a maximum number of 45 cigarettes smoked in one day. Mr. Jones' CO level averaged at 5.5% with a maximum of 20.7% and stayed above 4% for 60% of duration of the five-day evaluation period. Mr. Jones' triggers included work, home stressors, and commute. The report recommends a high dose and frequency nicotine level prediction for commencing nicotine replacement therapy in view of Mr. Jones' smoking habits. This may enable a higher likelihood of patient compliance in the quit program if the therapeutic regimen is customized to the patient needs from the outset.

In some embodiments, the data collected during the five-day evaluation, while the patient is smoking as usual and prior to the quit program, is used to establish a baseline for a patient's vital signs, e.g., CO, eCO, SpCO level. The system may generate a baseline curve for the patient's vital signs based on variance in CO, eCO, SpCO levels in the collected data. The baseline curve may serve as a reference for comparing against future measurements of the patient's CO, eCO, SpCO levels.

In some embodiments, the patient works with their doctor or counselor to begin the process to enter the quit program. Having the objective data in front of the doctor and patient may assist in set up for the quit program and for setting drug and counseling plans. In some embodiments, the system sets up a quit program automatically based on the data from the evaluation period. The collected data may impact the quit program initiation and set-up for the patient immediately before they enter the program by assisting in drug selection and dosing. For example, indication of higher and frequent smoking may prompt starting on higher nicotine replacement therapy dose or multiple drugs (e.g., adding medication used to treat nicotine addiction, such as varenicline).

The collected data may impact the quit program initiation and set-up by determining frequency, type, and duration of counseling required for the patient. The data may lead to stratification of smoker needs. For example, highest risk smokers with highest use may get more interventions while lower risk smokers may get fewer interventions. Interventions may include a text message, a phone call, a social networking message, or another suitable event, from the patient's spouse, friend, doctor, or another suitable stakeholder, at certain times of days when the patient is likely to smoke.

The collected data may impact the quit program initiation and set-up by correlating smoking behavior with all variables above such as stressors prompting smoking, time of day, and other suitable variables used for counseling the patient up front to be aware of these triggers. Counseling interventions may target these stressors. Interventions may be targeted at those times of day for the patient, such as a text message or phone call at those times of day. The collected data may impact the quit program initiation and set-up by assigning peer groups based on smoking behavior. The collected data may be used to predict and/or avert a smoking event. For example, if tachycardia or heart rate variability precedes most smoking events, this may sound an alarm and the patient may administer a dose of drug or can receive a phone call from a peer group, a doctor, or a counselor thereby averting a smoking event.

In some embodiments, the systems and methods described herein provide for maintaining participation in the quit program for the patient. Once in the quit program, the patient may continue to wear the wearable device for monitoring. The system may employ analytic tools such as setting an CO, eCO, SpCO baseline and tracking progress against this baseline. For example, the trend may drop to zero and stay there (indicating no more smoking). The trend may drop slowly with peaks and valleys (indicating reduction in smoking). The trend may drop to zero then spike for a recurrence (indicating a relapse).

The system may present the process for the patient as a game and improve visibility of progress. For example, the system may provide the patient with a small reward in exchange for abstaining from smoking for a certain period of time. In some embodiments, the system may transmit the data in real time to a health care provider for remote monitoring and allowing the provider to efficiently monitor and adjust patient care without having the patient present in the office every day.

In some embodiments, the systems and methods described herein provide for a follow up program after a patient successfully quits smoking. After a successful quit, verified by the system, the patient wears the wearable device for an extended period of time, e.g., a few months to two years, as an early detection system for relapse. The system may collect data and employ counseling strategies as described above for the quit program.

In some embodiments, the systems and methods described herein provide for a system comprising one or more mobile devices and a server in communication with the mobile devices. FIG. 1 shows an exemplary embodiment 100 for such a system including device 102, device 104, and server 106 in communication with devices 102 and 104. Device 102 assists in detecting a patient's smoking behavior. Device 102 includes a processor, a memory, and a communications link for sending and receiving data from device 104 and/or server 106. Device 102 includes one or more sensors to measure the patient's smoking behavior based on measuring one or more of the patient's CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. For example, device 102 may include PPG-based sensors for measuring CO, eCO, SpCO and SpO2, electrocardiography-based sensors for measuring heart rate and blood pressure, acoustic signal processing-based sensors for measuring respiratory rate, wearable temperature sensors for measuring body temperature, electrodermal activity-based sensors for measuring skin conductance, electroencephalogram, implantable sensors placed in the skin, fat or muscle that measure CO and other variables, intra-oral CO sensors, ambient CO sensors, and other suitable sensors. These sensors may have a variety of locations on or in the body for optimal monitoring.

Device 102 may be carryable or wearable. For example, device 102 may be wearable in a manner similar to a wristwatch. In another example, device 102 may be carryable or wearable and attached to the finger tip, ear lobe, ear pinna, toe, chest, ankle, arm, a fold of skin, or another suitable body part. Device 102 may attach to the suitable body part via clips, bands, straps, adhesively applied sensor pads, or another suitable medium. For example, device 102 may be attached to a finger tip via a finger clip. In another example, device 102 may be attached to the ear lobe or ear pinna via an ear clip. In yet another example, device 102 may be attached to the toe via a toe clip. In yet another example, device 102 may be attached to the chest via a chest strap. In yet another example, device 102 may be attached to the ankle via an ankle band. In yet another example, device 102 may be attached to the arm via bicep or tricep straps. In yet another example, device 102 may be attached to a fold of skin via sensor pads.

Device 102 may prompt the patient for a sample or the device, if worn, may take a sample without needing patient volition. The sampling may be sporadic, continuous, near continuous, periodic, or based on any other suitable interval. In some embodiments, the sampling is continuously performed as often as the sensor is capable of making the measurement. In some embodiments, the sampling is performed continuously after a set time interval, such as five or fifteen minutes or another suitable time interval.

In some embodiments, device 102 includes one or more sensors to monitor SpCO using a transcutaneous method such as PPG. The transcutaneous monitoring may employ transmissive or reflectance methods. Device 104 may be a smart phone or another suitable mobile device. Device 104 includes a processor, a memory, and a communications link for sending and receiving data from device 102 and/or server 106. Device 104 may receive data from device 102. Device 104 may include an accelerometer, a global positioning system-based sensor, a gyroscopic sensor, and other suitable sensors for tracking the described parameters. Device 104 may measure certain parameters, including but not limited to, movement, location, time of day, patient entered data, and other suitable parameters The patient entered data received by device 104 may include stressors, life events, geographic location, daily events, administrations of nicotine patches or other formulas, administrations of other drugs for smoking cessation, and other suitable patient entered data. For example, some of the patient entered data may include information regarding phone calls, athletics, work, sport, stress, sex, drinking, smoking, and other suitable patient entered data. Patient use of their smart phone for texting, calling, surfing, playing games, and other suitable use may also be correlated with smoking behavior, and these correlations leveraged for predicting behavior and changing behavior. Device 104 or server 106 (subsequent to receiving the data) may compile the data, analyze the data for trends, and correlate the data either real time or after a specified period of time is complete. Server 106 includes a processor, a memory, and a communications link for sending and receiving data from device 102 and/or device 104. Server 106 may be located remote to devices 102 and 104 at, e.g., a healthcare provider site, or another suitable location.

Figure 2:
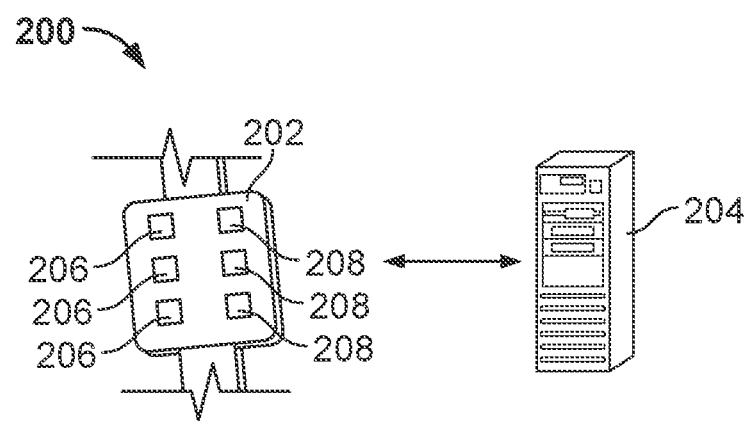
FIG. 2 depicts another illustrative system including a wearable device and a remote server in communication with the wearable device in accordance with some embodiments of the disclosure.

FIG. 2 shows an exemplary embodiment 200 for a system including device 202 and server 204 in communication with device 202. Device 202 assists in detecting a patient's smoking behavior. Device 202 includes a processor, a memory, and a communications link for sending and receiving data from server 204. Device 202 may be carryable or wearable. For example, device 202 may be wearable in a manner similar to a wristwatch. Device 202 includes one or more sensors 206 to measure the patient's smoking behavior based on measuring one or more of the patient's CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters.

Device 202 may include one or more sensors 208 to measure certain parameters, including but not limited to, movement, location, time of day, patient entered data, and other suitable parameters. The patient entered data may include stressors, life events, location, daily events, administrations of nicotine patches or other formulas, administrations of other drugs for smoking cessation, and other suitable patient entered data. The patient entered data may be received in response to a prompt to the patient on, e.g., a mobile device such as device 104, or entered without prompting on the patient's volition. For example, some of the patient entered data may include information regarding phone calls, athletics, work, sport, stress, sex, drinking, smoking, and other suitable patient entered data. Device 202 or server 204 (subsequent to receiving the data) may compile the data, analyze the data for trends, and correlate the data either real time or after a specified period of time is complete. Server 204 includes a processor, a memory, and a communications link for sending and receiving data from device 202. Server 204 may be located remote to device 202 at, e.g., a healthcare provider site, or another suitable location.

In some embodiments, device 102 or 202 includes a detector unit and a communications unit. Device 102 or 202 may include a user interface as appropriate for its specific functions. The user interface may receive input via a touch screen, keyboard, or another suitable input mechanism. The detector unit includes at least one test element that is capable of detecting a substance using an input of a biological parameter from the patient that is indicative of smoking behavior. The detector unit analyzes the biological input from the patient, such as expired gas from the lungs, saliva, or wavelengths of light directed through or reflected by tissue. In some embodiments, the detector unit monitors patient SpCO using PPG. The detector unit may optionally measure a number of other variables including, but not limited to, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. For breath-based sensors, patient input may include blowing into a tube as part of the detector unit. For saliva or other body fluid-based sensors, patient input may include placement of a fluid sample in a test chamber provided in the detector unit.

For light-based sensors such as PPG, patient input may include placement of an emitter-detector on a finger or other area of exposed skin. The detector unit logs the date and time of day, quantifies the presence of the targeted substance, and stores the data for future analysis and/or sends the data to another location for analysis, e.g., device 104 or server 106. The communications unit includes appropriate circuitry for establishing a communications link with another device, e.g., device 104, via a wired or wireless connection. The wireless connection may be established using WI-FI, BLUETOOTH, radio frequency, or another suitable protocol.

Figure 3:
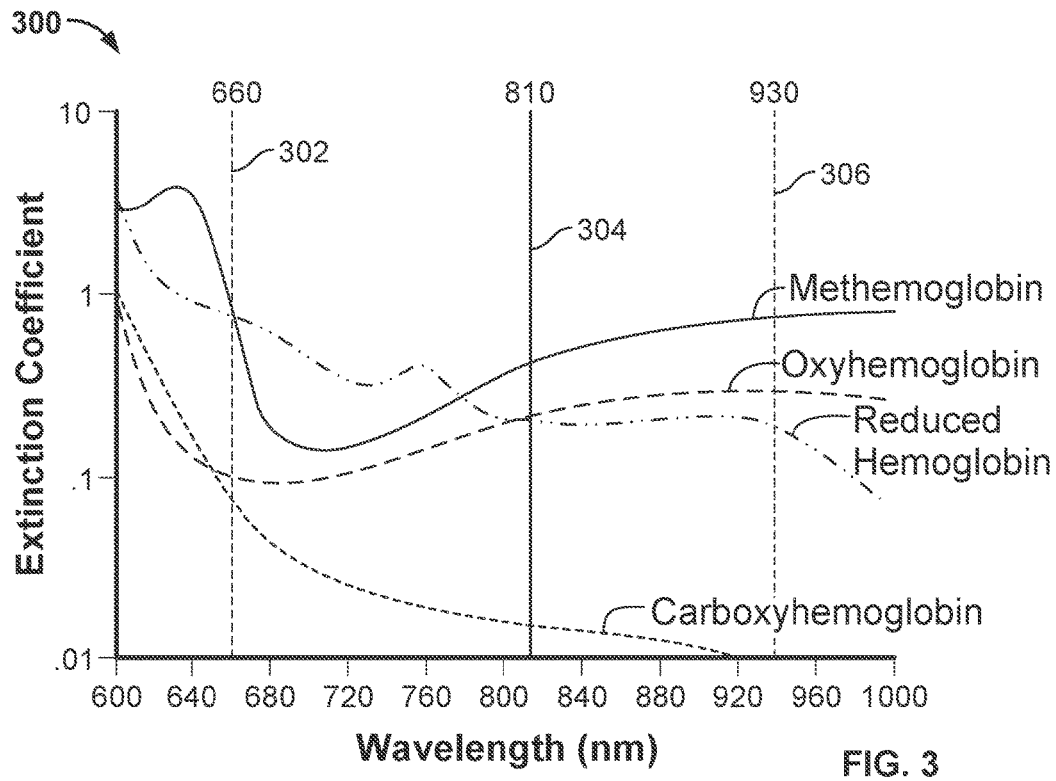
FIG. 3 depicts illustrative light absorption curves for various types of hemoglobin, allowing for measurement of the levels of carboxyhemoglobin (SpCO) and oxyhemoglobin (SpO2) using a photoplethysmography (PPG) sensor in accordance with some embodiments of the disclosure.

FIG. 3 depicts an illustrative embodiment 300 of suitable wavelengths for analyzing SpO2 and SpCO using a light-based sensor. SpCO for a patient may be measured by intermittently testing the patient's exhaled breath with a suitable sensor. In another example, SpCO for the patient may be measured using a transcutaneous method such as photoplethysmography (PPG). SpCO is detected by passing light through patient tissue, e.g., ear lobe, ear pinna, finger tip, toe, a fold of skin, or another suitable body part, and analyzing attenuation of various wavelengths. SpO2 is typically measured using two wavelengths, e.g., 302 (660 nm) and 306 (940 nm). SpCO may be measured using three wavelengths, e.g., 302 (660 nm), 304 (810 nm), and 306 (940 nm), or up to seven or more wavelengths, e.g., ranging from 500-1000 nm. Such a PPG sensor may be implemented via finger clips, bands, adhesively applied sensor pads, or another suitable medium. The PPG sensor may be transmissive, such as used in many pulse oximeters. In transmissive PPG sensors, two or more waveforms of light are transmitted through patient tissue, e.g., a finger, and a sensor/receiver on the other side of the target analyzes the received waveforms to determine SpCO. Alternatively, the PPG sensor may be reflective. In reflectance PPG sensors, light is shined against the target, e.g., a finger, and the receiver/sensor picks up reflected light to determine the measurement of SpCO. More details are provided below.

Transcutaneous or transmucosal sensors are capable of non-invasively determining blood CO level and other parameters based on analysis of the attenuation of light signals passing through tissue. Transmissive sensors are typically put against a thin body part, such as the ear lobe, ear pinna, finger tip, toe, a fold of skin, or another suitable body part. Light is shined from one side of the tissue and detected on the other side. The light diodes on one side are tuned to a specific set of wavelengths. The receiver or detector on the other side detects which waveforms are transmitted and how much they are attenuated. This information is used to determine the percentage binding of O2 and/or CO to hemoglobin molecules, i.e., SpO2 and/or SpCO.

Reflectance sensors may be used on a thicker body part, such as the wrist. The light that is shined at the surface is not measured at the other side but instead at the same side in the form of light reflected from the surface. The wavelengths and attenuation of the reflected light is used to determine SpO2 and/or SpCO. In some embodiments, issues due to motion of the patient wrist are corrected using an accelerometer. For example, the information from the accelerometer is used to correct errors in the SpO2 and SpCO values due to motion. Examples of such sensors are disclosed in U.S. Pat. No. 8,224,411, entitled "Noninvasive Multi-Parameter Patient Monitor." Another example of a suitable sensor is disclosed in U.S. Pat. No. 8,311,601, entitled "Reflectance and/or Transmissive Pulse Oximeter". These two U.S. patents are incorporated by reference herein in their entireties, including all materials incorporated by reference therein.

In some embodiments, device 102 or 202 is configured to recognize a unique characteristic of the patient, such as a fingerprint, retinal scan, voice label or other biometric identifier, in order to prevent having a surrogate respond to the signaling and test prompts to defeat the system. For this purpose, a patient identification sub-unit may be included in device 102 or 202. Persons of ordinary skill in the art may configure the identification sub-unit as needed to include one or more of a fingerprint scanner, retinal scanner, voice analyzer, or face recognition as are known in the art. Examples of suitable identification sub-units are disclosed, for example in U.S. Pat. No. 7,716,383, entitled "Flash-interfaced Fingerprint Sensor," and U.S. Patent Application Publication No. 2007/0005988, entitled "Multimodal Authentication," each of which is incorporated by reference herein in their entirety.

The identification sub-unit may include a built in still or video camera for recording a picture or video of the patient automatically as the biological input is provided to the test element. Regardless of the type of identification protocol used, device 102 or 202 may associate the identification with the specific biological input, for example by time reference, and may store that information along with other information regarding that specific biological input for later analysis.

A patient may also attempt to defeat the detector by blowing into the detector with a pump, bladder, billows, or other device, for example, when testing exhaled breath. In the embodiment of saliva testing, a patient may attempt to substitute a clean liquid such as water. For light based sensors, the patient may ask a friend to stand in for him or her. Means to defeat these attempts may be incorporated in to the system. For example, device 102 or 202 may incorporate the capability of discerning between real and simulated breath delivery. This functionality may be incorporated by configuring the detector unit to sense oxygen and carbon dioxide, as well as the target substance (e.g., carbon monoxide). In this manner, the detector unit can confirm that the gas being analyzed is coming from expired breath having lower oxygen and higher carbon dioxide than ambient air. In another example, the detector unit may be configured to detect enzymes naturally occurring in saliva so as to distinguish between saliva and other liquids. In yet another example, light based sensors may be used to measure blood chemistry parameters other than CO level and thus results may be compared to known samples representing the patient's blood chemistry.

In some embodiments, device 104 (e.g., a smart phone) receives measurements from device 102 (e.g., a wearable device) in real time, near real time, or periodically according to a suitable interval. Device 104 may provide a user interface for prompting a patient for certain inputs. Device 104 may provide a user interface for displaying certain outputs of the collected data. Device 104 may permit the patient to input information that the patient believes relevant to his or her condition without prompting or in response to prompting. Such information may include information about the patient's state of mind such as feeling stressed or anxious. Such unprompted information may be correlated to a biological input based on a predetermined algorithm, such as being associated with the biological input that is closest in time to the unprompted input, or associated with the first biological input occurring after the unprompted input. Server 106 (e.g., a healthcare database server) may receive such data from one or both of devices 102 and 104. In some embodiments, the data may be stored on a combination of one or more of devices 102, 104, and 106. The data may be reported to various stakeholders, such as the patient, patient's doctor, peer groups, family, counselors, employer, and other suitable stakeholders.

In some embodiments, a wearable device, e.g., device 102 or 202, may be applied to patients during, e.g., their usual annual visits, to detect smoking behavior and then refer the smokers to quit programs. The patient is provided with a wearable device to wear as an outpatient for a period of time, e.g., one day, one week, or another suitable period of time.

Figure 7:
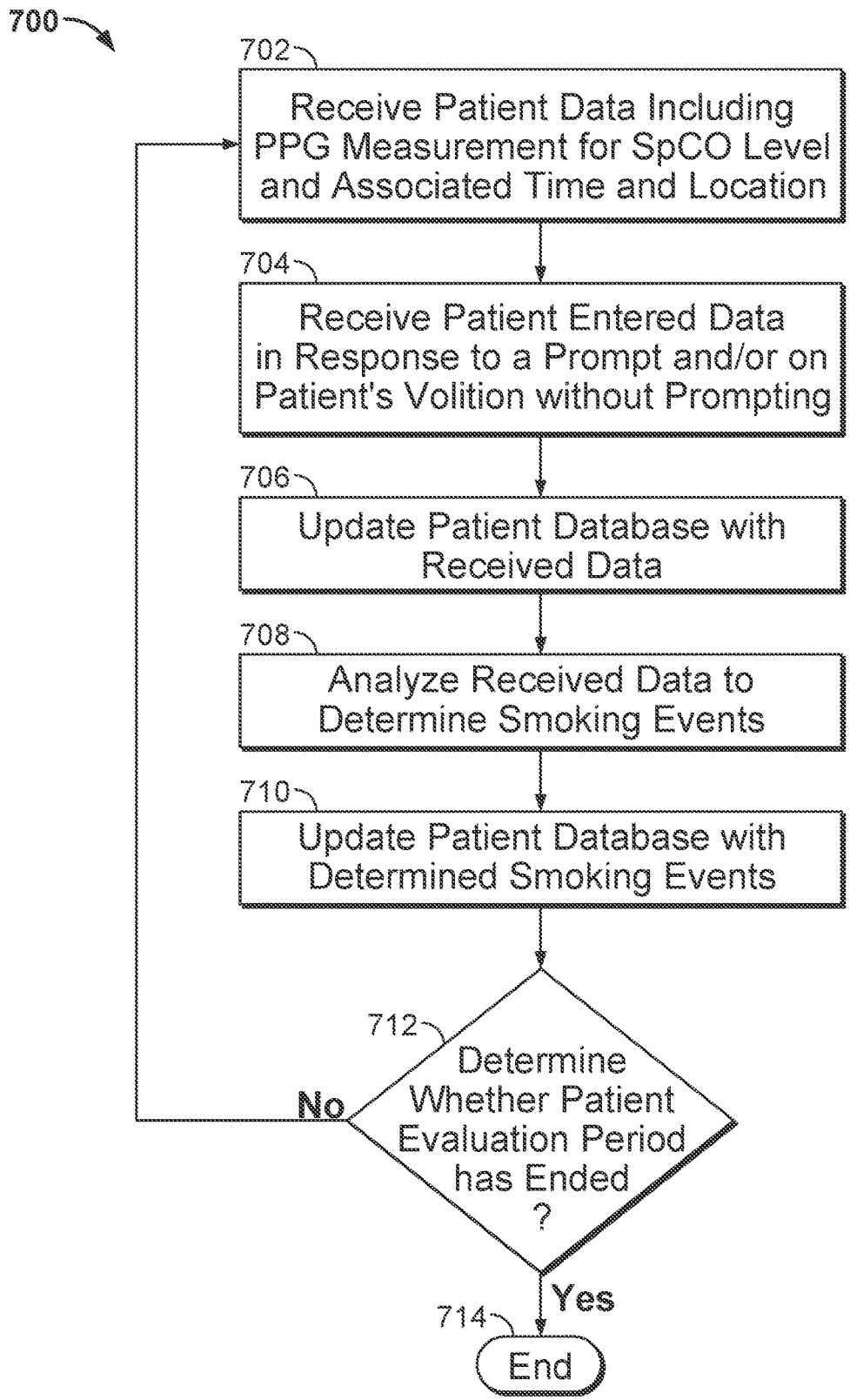
FIG. 7 depicts an illustrative flow diagram for detecting smoking behavior of a patient in accordance with some embodiments of the disclosure.

Longer wear times may provide more sensitivity in detection of smoking behavior and more accuracy in quantifying the variables related to smoking behavior. FIG. 7 below provides an illustrative flow diagram for detecting smoking behavior and will be described in more detail below.

In some embodiments, employers ask employees to voluntarily wear the wearable device for a period of time, such as one day, one week, or another suitable period of time. The incentive program may be similar to programs for biometric screening for obesity, hyperlipidemia, diabetes, hypertension, and other suitable health conditions. In some embodiments, health care insurance companies ask their subscribers to wear the wearable device for a suitable period of time to detect smoking behavior. Based on the smoking behavior being quantified, these patients may be referred to a smoking cessation program as described in the present disclosure.

Figure 4:
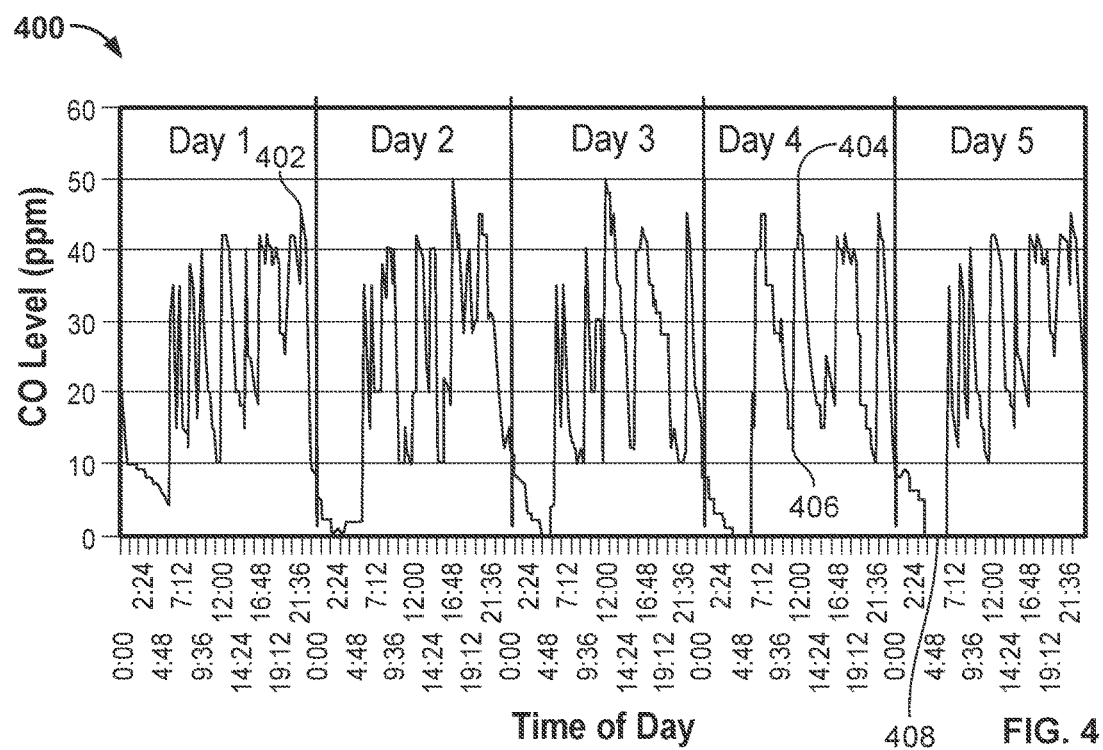
FIG. 4 depicts a chart for a patient's varying levels of SpCO for a typical five-day monitoring period prior to commencing a smoking cessation program in accordance with some embodiments of the disclosure.

When wearing the wearable device for a suitable period of time, e.g., five days, a number of parameters may be measured real-time or near real time. These parameters may include, but are not limited to, CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. FIG. 4 shows illustrative chart 400 for a patient's varying levels of SpCO for a typical five-day monitoring period. Data points 402 and 404 indicate high level of CO which in turn likely indicates high smoking events. Data points 406 and 408 indicate low level of CO likely because the patient was asleep or otherwise occupied. One or more algorithms may be applied to the granular data points on the curve to detect a smoking event with adequate sensitivity and specificity. For example, the algorithms may analyze one or more of shape of the SpCO curve, start point, upstroke, slope, peak, delta, downslope, upslope, time of change, area under curve, and other suitable factors, to detect the smoking event.

Data from the wearable device may be sent to a smart phone, e.g., device 104, or a cloud server, e.g., server 106 or 204, either in real time, at the end of each day, or according to another suitable time interval. The smart phone may measure parameters, including but not limited to, movement, location, time of day, patient entered data, and other suitable parameters. The patient entered data may include stressors, life events, location, daily events, administrations of nicotine patches or other formulas, administrations of other drugs for smoking cessation, and other suitable patient entered data. For example, some of the patient entered data may include information regarding phone calls, athletics, work, sport, stress, sex, drinking, smoking, and other suitable patient entered data. The received data may be compiled, analyzed for trends, and correlated either real time or after the period of time is complete.

Figures 5, 6:
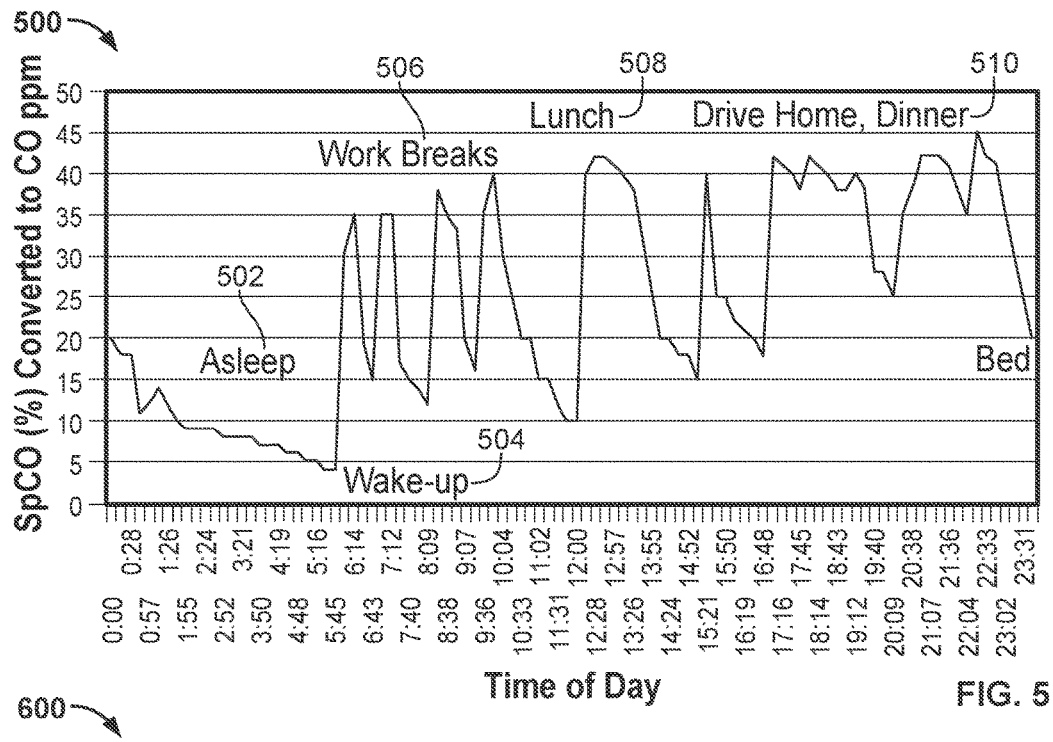
FIG. 5 depicts a trend of SpCO levels and smoking triggers for a patient over a typical day prior to commencing a smoking cessation program in accordance with some embodiments of the disclosure.
FIG. 6 depicts a data structure for storing SpCO levels and smoking triggers for a patient over a typical day in accordance with some embodiments of the disclosure.

From the parameters measured above, information regarding smoking may be derived via a processor located in, e.g., device 102, 104, or 202, or server 106 or 204. For example, the processor may analyze the information to determine CO trends, averages, peaks, and associations, other vital sign trends during day, and how do those vitals change before, during and after smoking. FIG. 5 shows an illustrative diagram 500 for the analyzed information. The patient may arrive at FIG. 5 by zooming in on a given day in FIG. 4. Data point 502 indicates the SpCO level when the patient is asleep. Data point 504 shows that when the patient wakes up, the SpCO level is the lowest. Data points 506, 508, and 510 indicate high SpCO levels are associated with triggers such as work breaks, lunch, and commute. The processor may analyze the SpCO trends in FIG. 5 to determine parameters such as total number of cigarettes smoked, average number of cigarettes smoked per day, maximum number of cigarettes smoked per day, intensity of each cigarette smoked, quantity of each cigarette smoked, what that patient's smoking event looks like on the curve to be used later for quit program, time of day, day of week, associated stressors, geography, location, and movement. For example, the total number of peaks in a given day may indicate the number of cigarettes smoked, while the gradient of each peak may indicate the intensity of each cigarette smoked.

FIG. 6 depicts an illustrative data structure for storing patient data. In this embodiment, data structure 600 illustrates patient data 602 associated with data points in FIG. 5, e.g., data point 508. Patient data 602 includes identifying information for the patient such as patient name 604 and patient age 606. Patient data 602 includes curve data 608 corresponding to the curve in FIG. 5. For example, curve data 608 includes curve identifier 610 corresponding to data point 508. The data corresponding to data point 508 may be collected by device 102, 104, or 202, and/or server 106 or 204 or a combination thereof. Data associated with curve identifier 610 includes day, time, and location information 612. The data includes patient vital signs such as CO and O2 levels 614. The data includes patient entered data such as trigger 616. The patient entered data may be entered in response to a prompt to the patient on, e.g., device 104, or entered without prompting on the patient's volition. Curve data 608 includes curve identifier 618 for additional data points in FIG. 5. Data structure 600 may be adapted as appropriate for storing patient data.

FIG. 7 depicts an illustrative flow diagram 700 for detecting smoking behavior of a patient over a suitable evaluation period. When the patient wears the wearable device for a suitable period of time, e.g., five days, a number of parameters may be measured in real-time, near real time, at the end of each day, or according to another suitable time interval. These parameters may include, but are not limited to, CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. The wearable device or another suitable device may measure parameters, including but not limited to, movement, location, time of day, and other suitable parameters.

At step 702, a processor in a smart phone, e.g., device 104, or a cloud server, e.g., server 106 or 204, receives the described patient data. At step 704, the processor receives patient entered data in response to a prompt displayed to the patient on, e.g., a smart phone, and/or patient data entered without a prompt on the patient's volition. The patient entered data may include stressors, life events, location, daily events, administrations of nicotine patches or other formulas, administrations of other drugs for smoking cessation, and other suitable patient entered data. At step 706, the processor sends instructions to update a patient database with the received data. For example, the processor may transmit the patient data to a healthcare provider server or a cloud server that hosts the patient database.

At step 708, the processor analyzes the patient data to determine smoking events. The processor may compile the data, analyze the data for trends, and correlate the data either real time or after the evaluation period is complete. For example, the processor may analyze the information to determine CO trends, averages, peaks, shape of curve, and associations, other vital sign trends during day, and how those vitals change before during and after smoking. The processor may analyze the SpCO trends to determine parameters such as total number of cigarettes smoked, average number of cigarettes smoked per day, maximum number of cigarettes smoked per day, intensity of each cigarette smoked, time of day, day of week, associated stressors, geography, location, and movement. For example, the total number of peaks in a given day may indicate the number of cigarettes smoked, while the gradient of each peak may indicate the intensity of each cigarette smoked.

At step 710, the processor transmits the determined smoking events and related analysis to the patient database for storage. At step 712, the processor determines whether the evaluation period has ended. For example, the evaluation period may be five days or another suitable time period. If the evaluation period has not ended, the processor returns to step 702 to receive additional patient data, analyze the data, and update the patient database accordingly.

If the evaluation period has ended, at step 714, the processor ends the data collection and analysis. For example, the processor may evaluate all collected data at the end of the evaluation period to prepare a report as described with respect to FIG. 8 below.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 1 (e.g., device 102, 104, or 106) or FIG. 2 (e.g., device 202 or 204) could be used to perform one or more of the steps in FIG. 7.

Figure 8:
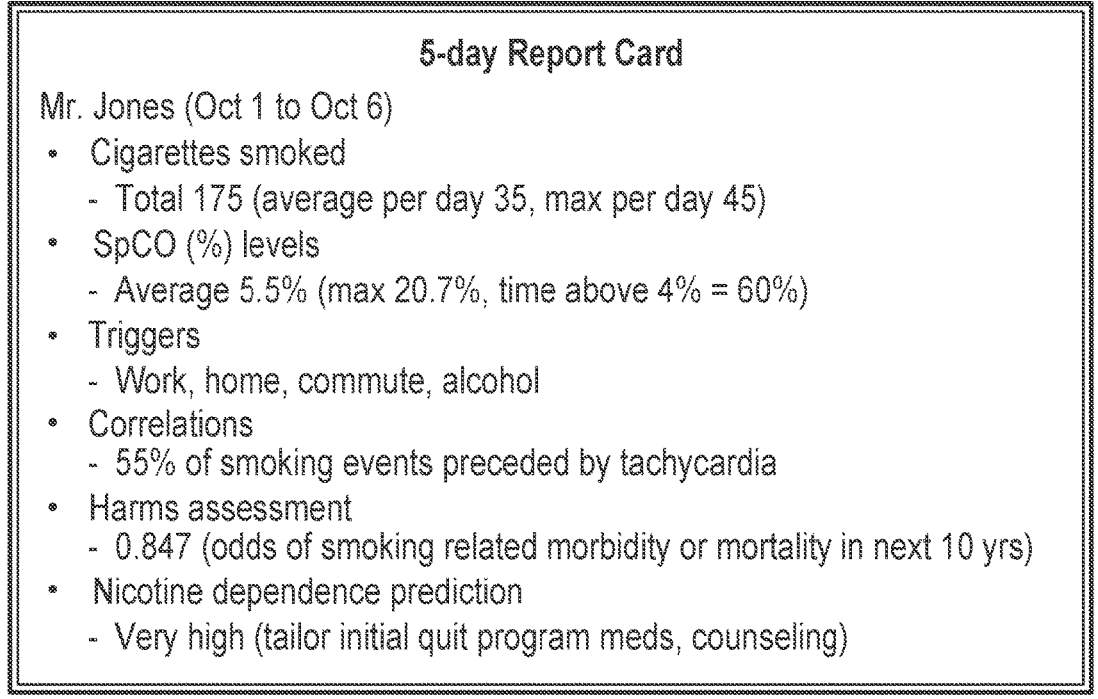
FIG. 8 depicts a sample report after a five-day evaluation for a patient in accordance with some embodiments of the disclosure.

In some embodiments, the systems and methods described herein provide for initiating and setting up a quit program for a patient. After the patient has completed a five-day evaluation while wearing the wearable device, e.g., device 102 or 202, the full dataset is compiled and analyzed by the system and delivered to the patient or a doctor for the quit program. FIG. 8 shows an illustrative embodiment 800 of a sample report from the analysis. For example, the report indicates that, from October 1 to October 6, Mr. Jones smoked a total of 175 cigarettes with an average number of 35 cigarettes smoked per day, and a maximum number of 45 cigarettes smoked in one day. Mr. Jones' CO level averaged at 5.5% with a maximum of 20.7% and stayed above 4% for 60% of duration of the five-day evaluation period. Mr. Jones' triggers included work, home stressors, and commute. The report recommends a high dose and frequency nicotine level prediction for commencing nicotine replacement therapy in view of Mr. Jones' smoking habits.

In some embodiments, the patient works with their doctor or counselor to begin the process to enter the quit program. In some embodiments, the system sets up a quit program automatically based on the data from the evaluation period. The sample report in FIG. 8 is one example of measuring SpCO and producing a report on CO exposure, associated stressors, and predicting a starting nicotine dose requirement. For example, a high volume and intensity smoker may be more nicotine dependent at quit program entry, which the processor can estimate based on five-day behavior, and the quit program would start the patient on a higher nicotine replacement therapy dose. This may avoid many patients failing early in a quit program due to withdrawal symptoms.

Based on the report data, including average and maximum number of cigarettes smoked, SpCO levels, triggers, the processor may determine the dosage for nicotine for administration to the patient. For example, the processor may determine a high dosage of nicotine for patients that on average smoke more than a threshold number of cigarettes per day. As the report data is updated, the processor may update the dosage for nicotine as well.

The collected data may impact the quit program initiation and set-up for the patient immediately before they enter the program by assisting in drug selection and dosing. For example, indication of higher smoking may prompt starting on higher nicotine replacement therapy dose or multiple drugs (e.g., adding medication used to treat nicotine addiction, such as varenicline). The collected data may impact the quit program initiation and set-up by determining frequency, type, and duration of counseling required for the patient. The data may lead to stratification of smoker needs. For example, highest risk smokers with highest use may get more interventions while lower risk smokers may get fewer interventions. For example, interventions may include a text message, a phone call, a social networking message, or another suitable event, from the patient's spouse, friend, doctor, or another suitable stakeholder, at certain times of days when the patient is likely to smoke.

Figure 14:
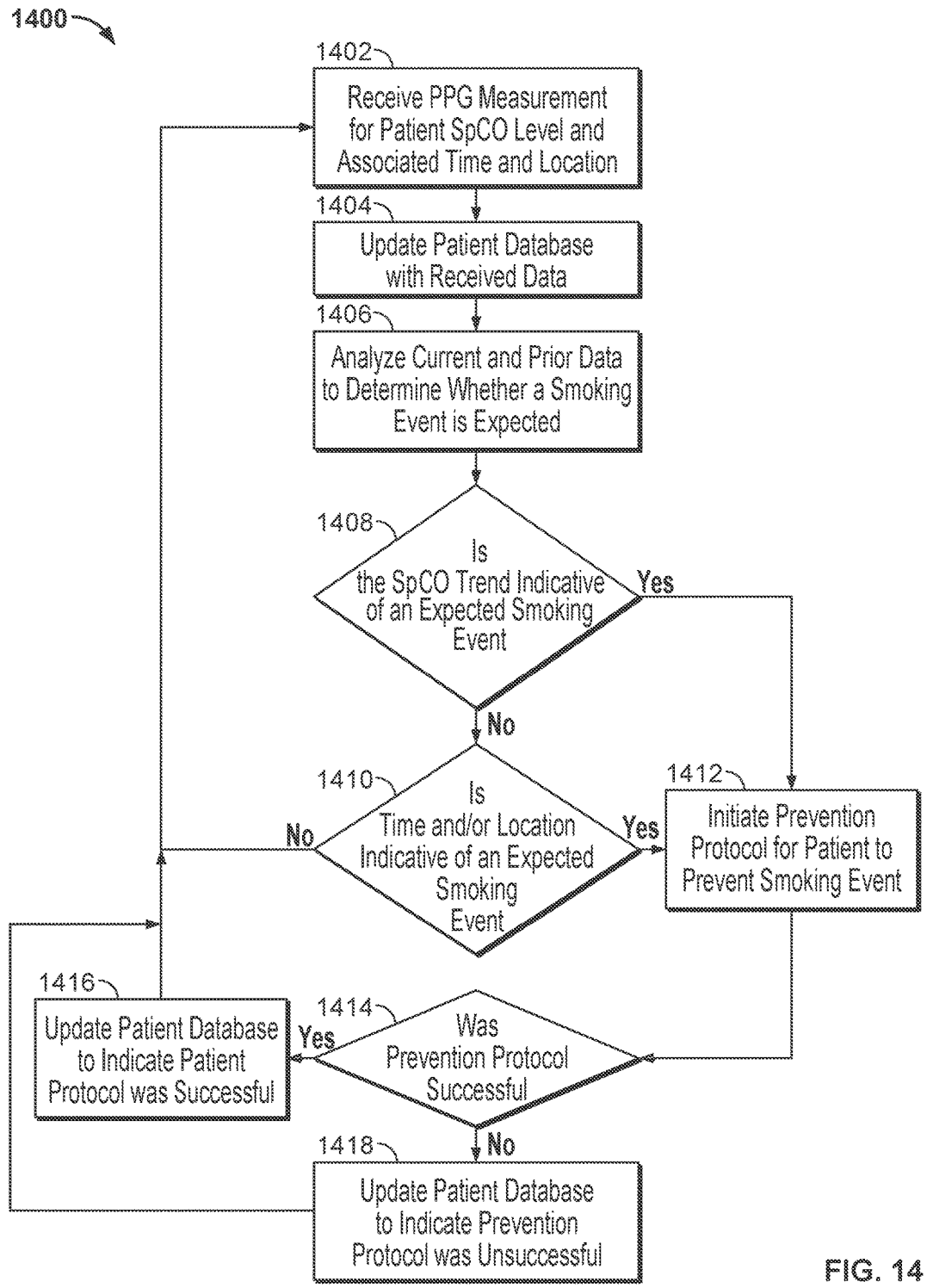
FIG. 14 depicts an illustrative flow diagram for predicting and preventing an expected smoking event in accordance with some embodiments of the disclosure.
Figure 15:
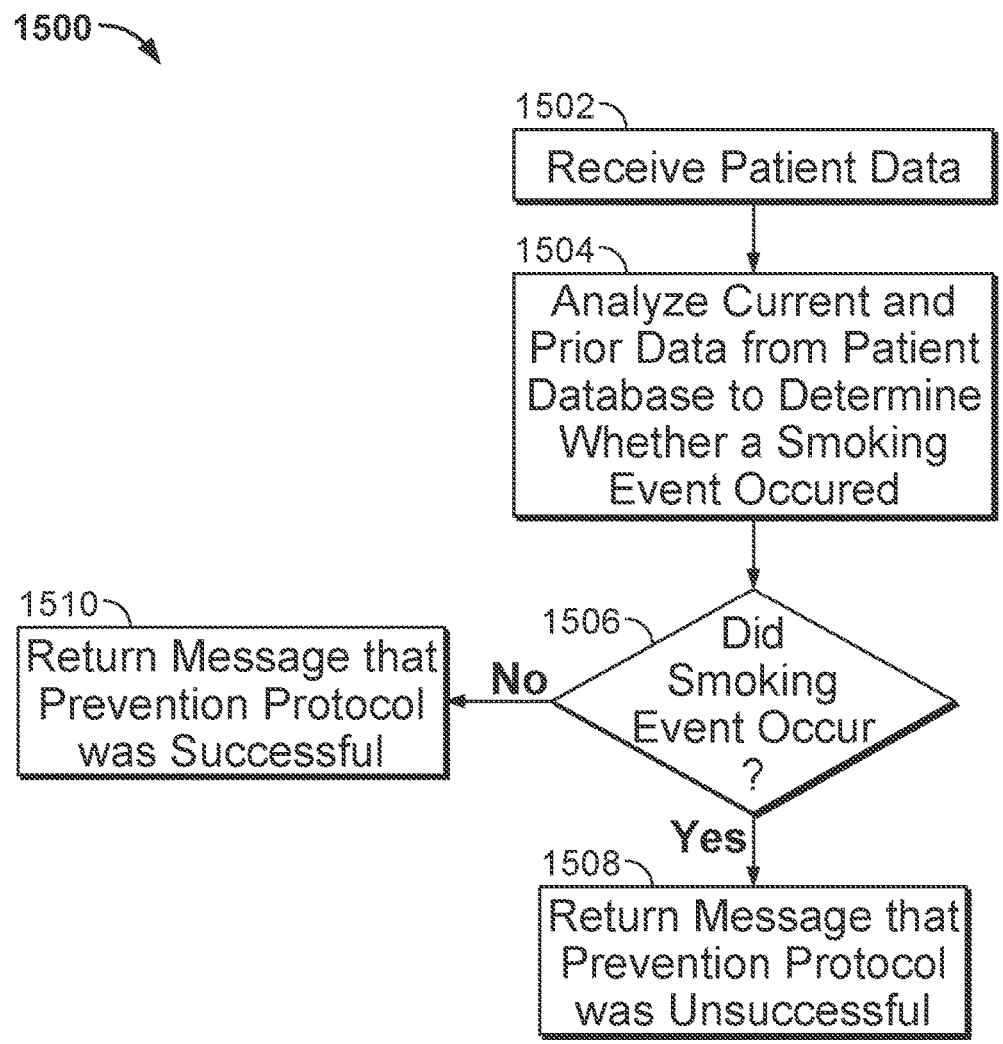
FIG. 15 depicts an illustrative flow diagram for step 1414 in FIG. 14 for determining whether a prevention protocol was successful in accordance with some embodiments of the disclosure.

The collected data may impact the quit program initiation and set-up by correlating smoking behavior with all variables above such as stressors prompting smoking, time of day, and other suitable variables used for counseling the patient up front to be aware of these triggers. Counseling interventions may target these stressors and there may be interventions aimed at those times of day for the patient, such as a text message or call at those times of days. The collected data may impact the quit program initiation and set-up by assigning peer groups based on smoking behavior. The collected data may be used to predict and/or avert a smoking event. For example, if tachycardia or heart rate variability or a suitable set of variables precedes most smoking events, this will sound an alarm and the patient may administer a dose of drug or can receive a call from a peer group, doctor, or counselor. FIG. 12 shows an illustrative embodiment of preempting a smoking event and will be discussed in more detail below. FIGS. 14 and 15 show illustrative flow diagrams for predicting and preventing an expected smoking event and will be discussed in more detail below.

In some embodiments, the systems and methods described herein provide for maintaining participation in the quit program for the patient. Once in the quit program, the patient may continue to wear the wearable device, e.g., device 102 or 202, for monitoring. The system may employ analytic tools such as setting an SpCO baseline and tracking progress against this baseline. The trend may drop to zero and stay there (indicating no more smoking). The trend may drop slowly with peaks and valleys (indicating reduction in smoking). The trend may drop to zero then spike for a recurrence (indicating a relapse).

The system may employ patient engagement strategies by providing small infrequent rewards for group or individual progress to engage the patient. The system may provide employer rewards, payers, spouse, or peer groups to engage the patient. The system may present the process for the patient as a game and improve visibility of progress. FIG. 13 provides an illustrative embodiment of such a user interface and will be discussed in more detail below. In some embodiments, the system may transmit the data in real time to a health care provider for remote monitoring and allowing the provider to efficiently monitor and adjust patient care without having to have them in the office every day. For example, the provider may send instructions to the system to adjust medication type and dose, alter intensity of counseling, call and text for positively encouraging progress, or trigger an intervention if the patient is failing to refrain from smoking. This may supplant staffed quit phone lines which are expensive and may efficiently automate the process. The system may employ increased intensity and frequency to improve outcomes in patients. The system may encourage the patient via support from spouse, employer, health care provider, peers, friends, and other suitable parties via scheduled phone calls, text messages, or other suitable communications.

Figure 9:
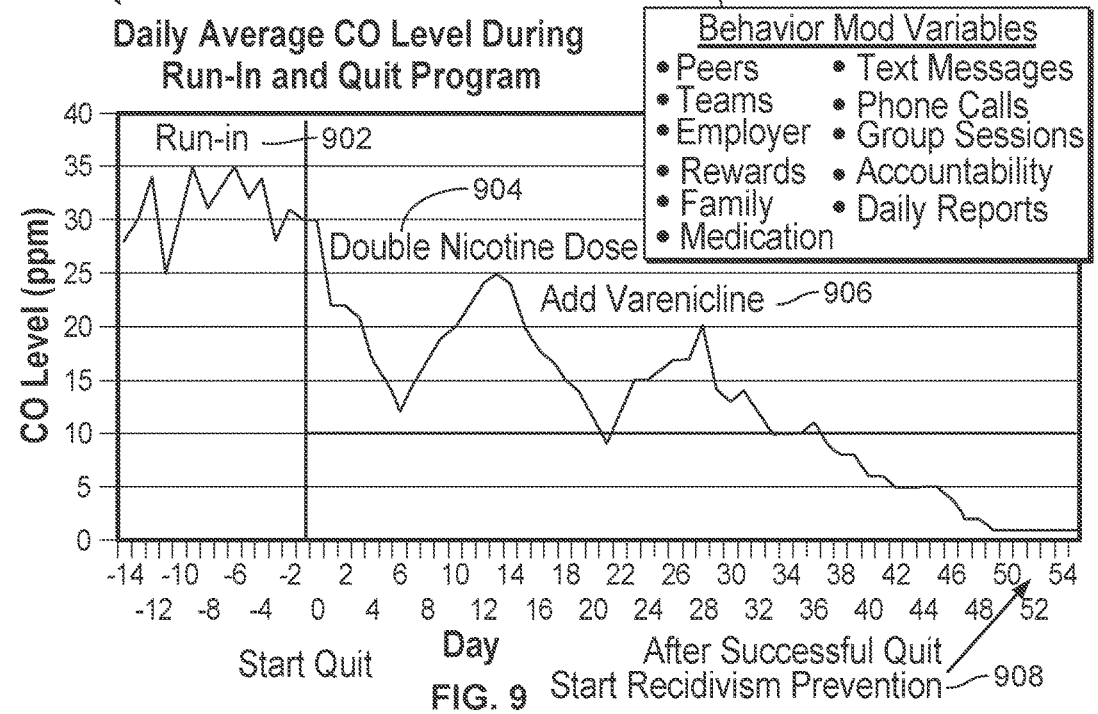
FIG. 9 depicts an illustrative chart of patient SpCO levels during run-in and quit program in accordance with some embodiments of the disclosure.

FIG. 9 shows an illustrative graph 900 for tracking the average daily SpCO trend for a patient running up to and then entering a quit program. The average trend is tracked for each day as it improves. The doctor or counselor may zoom in on a particular day (present or past) to see the granular detail and associations of CO with other parameters measured and associated stressors 910. Visibility of the trend of CO over time in the quit program may prevent patient dropouts, prevent smoking relapse, titrate drugs and counseling, and improve outcomes. For example data point 902 indicates CO level before the patient entered the quit program. Data points 904 and 906 indicate CO levels as nicotine replacement therapy and varenicline therapy is administered during the quit program. Data point 908 indicates the patient has successfully quit smoking. At this point, the system may recommend the patient enter into a recidivism prevention program to prevent relapse.

In some embodiments, the systems and methods described herein provide for a follow up program after a patient successfully quits smoking. After a successful quit, verified by the system, the patient wears the wearable device, e.g., device 102 or 202, for an extended period of time, e.g., a few months to two years, as an early detection system for relapse. The system may collect data and employ counseling strategies as described above for the quit program.

In some embodiments, a patient receives a wearable device, e.g., device 102 or 202, and an app for their smartphone, e.g., device 104, that allows them to assess health remotely and privately by tracking several different parameters. The patient may submit breath samples or put their finger in or on a sensor on the wearable device several times per day as required. They may wear the wearable device to get more frequent or even continuous measurements. At the end of a test period, e.g., five to seven days or another suitable time period, the processor in the smart phone may calculate their CO exposure and related parameters. FIG. 10 shows an exemplary app screen 1000 showing measurements such as SpCO 1002, SpO2 1004, heart rate 1006, respiratory rate 1008, blood pressure 1010, and body temperature 1012. Warning indicators 1014 and 1016 may be provided for atypical measurements, possibly indicating effects of smoking on the body. The system may prompt the patient with alerts when warning indicators 1014 or 1016 are activated.

The system may recommend the patient enter a smoking cessation program and provide options for such programs. The patient may agree to enter a quit program on seeing such objective evidence of smoking. The system may share this data with the patient's spouse, their doctor, or another suitable stakeholder involved in the patient's quit program. For example, the system may share the data with an application a stakeholder's mobile device or send a message including the data via email, phone, social networking, or another suitable medium. Triggers to get a patient to join the quit program may include spousal suggestion, employer incentive, peer pressure, personal choice, an illness, or another suitable trigger. The patient may initiate the quit program on their own or bring the data to a doctor to receive assistance in joining a quit program.

While the patient is initiated in the quit program, the wearable device, e.g., device 102 or 202, may continue to monitor the patient's health parameters, such as heart rate, movement, location that precede the smoking behavior, and transmit the data to the patient and/or his doctor to improve therapy. The smart phone app on, e.g., device 104, may receive patient entered data including, but not limited to, stressors, life events, location, daily events, administrations of nicotine patches or other formulas, administrations of other drugs for smoking cessation, and other suitable patient entered data.

FIG. 11 shows an illustrative embodiment of an app screen 1100 for receiving patient entered data. App screen 1100 may be displayed when the smart phone app receives an indication of a smoking event, e.g., due to a spike in the CO level for the patient. App screen 1100 prompts the user to enter a trigger for the smoking event. For example, the patient may select from one of options 1102, 1104, 1106, and 1108 as triggering a smoking event or select option 1110 and provide further information regarding the trigger. Other triggers for a smoking event may include phone calls, athletics, sport, stress, sex, and other suitable patient entered data. The patient may voluntarily invoke app screen 1100 as well to enter trigger information for a smoking event. In some embodiments, app screen 1100 for receiving patient data is displayed to the patient during the five-day evaluation period to collect information regarding smoking behavior before the patient enters the quit program.

In some embodiments, the collected data is used by the smart phone app to avert a smoking event. The processor running the app or a processor in another device, such as device 102 or 202 or server 106 or 204, may analyze the information regarding what happens to heart rate and other vital signs in the period leading up to a smoking event. The processor may correlate changes in heart rate, such as tachycardia, that can predict when a patient will smoke. This information may be used to initiate a prevention protocol for stopping the smoking event. For example, the prevention protocol may include delivering a bolus of nicotine. The nicotine may be delivered via a transdermal patch or a transdermal transfer from a reservoir of nicotine stored in the wearable device, e.g., device 102 or 202. In another example, the prevention protocol may include calling the patient's doctor, a peer group, or another suitable stakeholder. The processor may send an instruction to an automated call system, e.g., resident at server 106 or 204, to initiate the call. FIGS. 14 and 15 provide flow diagrams for predicting a smoking event based on patient vital signs and will be described in more detail below.

FIG. 12 shows an illustrative embodiment of an app screen 1200 implementing such a prevention protocol. For example, if a patient tends to become tachycardic twenty minutes before every cigarette, the processor may detect tachycardia and prompt the patient to administer nicotine via option 1202. The patient may vary the nicotine dose via option 1204. In some embodiments, the nicotine is administered automatically. The amount may be determined based on the patient's current SpCO level or another suitable parameter. The patient may receive a call from a peer group via option 1206, a doctor via option 1208, or another suitable stakeholder. The caller may provide the patient encouragement to abstain from smoking and suggest seeking out other activities to divert the patient's attention.

In some embodiments, the smart phone app presents the process for the patient as a game to improve visibility of progress. The app may employ patient engagement strategies by providing small frequent or infrequent rewards for group or individual progress to engage the patient. The app may provide employer rewards, payers, spouse, or peer groups to engage the patient. FIG. 13 shows an illustrative app screen 1300 for such an embodiment. App screen 1300 offers the patient a reward for abstaining from smoking for fifteen days. Prompt 1302 challenges the patient to further abstain for another fifteen days. The patient may select option 1304 to accept the reward and continue monitoring progress while he remains smoke free. However, the patient may be having difficulty abstaining and may select option 1306 to be contacted a peer group, a counselor, a family member, a doctor, or another suitable party.

In some embodiments, the patient is a peer and supporter for others in their group. Groups can track each other's progress and give support. For example, the group members may be part of a social network that allows them to view each other's statistics and provide encouragement to abstain from smoking. In another example, a message, e.g., a tweet, may be sent to group members of the patient's social network, e.g., followers, when it is detected the patient is smoking. The message may inform the group members that the patient needs help. The group may connect to the patient in a variety of ways to offer help. This interaction may enable to the patient to further abstain from smoking that day.

Figure 16:
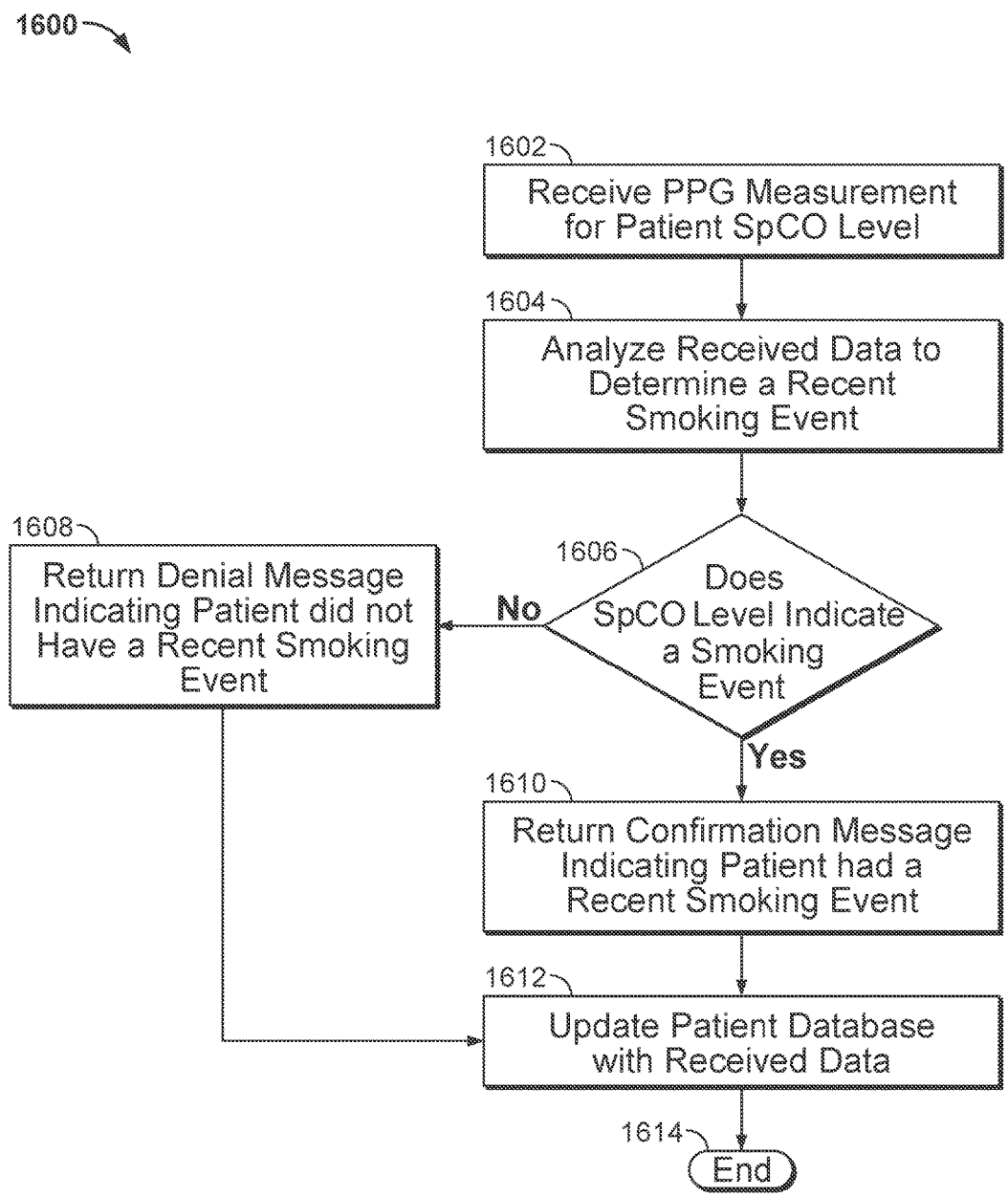
FIG. 16 depicts an illustrative flow diagram for a one time measurement of the patient's SpCO level using a PPG sensor in accordance with some embodiments of the disclosure.

In some embodiments, at a primary care visit a patient provides a sample and is asked if they smoke. For example, the wearable device, e.g., device 102 or 202, is applied to the patient and receives the sample for a one time on-the-spot measurement of the patient's SpCO level. The SpCO level may exceed a certain threshold which suggests that the patient smokes. FIG. 16 provides a flow diagram for the one time measurement of the patient's SpCO level. The patient may be provided with the wearable device to wear as an outpatient for a period of time, e.g., one day, one week, or another suitable period of time. Longer wear times may provide more sensitivity in detection of smoking behavior and more accuracy in quantifying the variables related to smoking behavior.

The wearable device, e.g., device 102 or 202, and smart phone app on, e.g., device 104, may continue to monitor the patient's health parameters, such as SpCO level, in real time or near real time and process the data for observation by the patient, the doctor, or any other suitable party. The smart phone app may also offer the data in a digestible form for daily or weekly consumption by the patient and/or the doctor. For example, the smart phone app may generate display similar to FIG. 9 showing daily progress with the option to zoom into a particular day for observing further details. The doctor may log the patient into a healthcare database stored at, e.g., server 106 or 204 in communication with a mobile device running the smart phone app, and continue to receive the data from the smart phone app via the Internet or another suitable communications link. The smart phone app may receive data from the sensors via a wired connection to the mobile device running the app or via a wireless connection such as WI-FI, BLUETOOTH, radio frequency, or another suitable communications link.

The patient and the doctor may set a future quit date and send the patient home without any drugs or with drugs to help the patient quit. The patient may begin working towards the agreed quit date. Feedback from the wearable device and/or the smart phone app may assist the patient to be more prepared at the quit date to actually quit as well as to smoke less at the quit date than when they started at the start. Once the patient starts the quit program, they may get daily or weekly feedback from their spouse, doctor, nurse, counselor, peers, friends, or any other suitable party.

Drug therapy, if prescribed, may be based by the doctor or may be adjusted automatically based on patient performance. For example, the doctor may remotely increase or decrease nicotine dose administration based on the patient's CO, eCO, SpCO level. In another example, a processor in the wearable device, e.g., device 102 or 202, the smart phone, e.g., device 104, or a remote server, e.g., server 106 or 204, may increase or decrease nicotine dose administration based on CO trends from the patient's past measurements. Similarly, the drug therapy may be shortened or lengthened in duration according to collected data.

FIG. 14 depicts an illustrative flow diagram 1400 for predicting a smoking event based on a patient's CO, eCO, SpCO measurements and other suitable factors. The patient may be given a wearable device, e.g., device 102 or 202, and a smart phone app for their mobile phone, e.g., device 104. The wearable device may include a PPG sensor for measuring the patient's SpCO level. At step 1402, a processor in the wearable device or the patient's mobile phone receives a PPG measurement for the patient's SpCO level and associated time and location. The processor may also receive other information such as heart rate, respiration rate, and other suitable factors in predicting a smoking event.

At step 1404, the processor updates a patient database that is stored locally or at a remote location, such as a healthcare database in server 106, with the received patient data. At step 1406, the processor analyzes the current and prior measurements for the patient parameters and determines whether a smoking event is expected. For example, the SpCO trend may be at a local minimum which indicates the user may be reaching for a cigarette to raise their SpCO level. The processor may apply a gradient descent algorithm to determine the local minimum. At step 1408, the processor determines whether the SpCO trend indicates an expected smoking event. If the processor determines a smoking event is not expected, at step 1410, the processor determines if the time and/or location are indicative of an expected smoking event. For example, the processor may determine that the patient typically smokes when they wake up in the morning around 7 a.m. In another example, the processor may determine that the patient typically smokes soon after they arrive at work. In yet another example, the processor may determine that the patient typically smokes in the evening whenever they visit a particular restaurant or bar.

If the processor determines a smoking event is expected from either steps 1408 or 1410, at step 1412, the processor initiates a prevention protocol for the patient to prevent the smoking event. Information regarding the prevention protocol may be stored in memory of device 102, 104, or 202, or server 106 or 204, or a combination thereof. The information for the prevention protocol may include instructions for one or more intervention options to initiate when the patient is about to smoke. For example, the processor may initiate an alarm in the patient's mobile phone and display an app screen similar to FIG. 12. The app screen may offer the patient options to administer nicotine or receive a call from a peer group, a doctor, or another suitable party. Alternatively, the prevention protocol may include automatically administering a bolus of nicotine to the patient from a reservoir of nicotine stored in the patient's wearable device.

In another example, the app screen may indicate that a message, e.g., a tweet, will be sent to group members of the patient's social network, e.g., followers, when it is detected the patient has failed to abstain from smoking. The patient may refrain from smoking to prevent the message indicating his failure from being sent out.

In some embodiments, steps 1408 and 1410 are combined into one step or include two or more steps for a processor determining that a smoking event is expected. For example, the processor may determine that a smoking event is expected based on a combination of the SpCO trend, the patient's location, and/or the current time. In another example, the processor may determine that a smoking event is expected based on a series of steps for analyzing one or more of the patient's SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters.

At step 1414, the processor determines whether the prevention protocol was successful. If a smoking event occurred, at step 1418, the processor updates the patient database to indicate that the prevention protocol was not successful. If a smoking event did not occur, at step 1416, the processor updates the patient database to indicate that the prevention protocol was successful. The processor returns to step 1402 to continue receiving the PPG measurement for the patient's SpCO level and associated data. The processor may monitor the patient's vital signs continuously to ensure that the patient does not relapse into a smoking event.

It is contemplated that the steps or descriptions of FIG. 14 may be used with any other embodiment of this disclosure. In addition, the steps and descriptions described in relation to FIG. 14 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 1 (e.g., device 102, 104, or 106) or FIG. 2 (e.g., device 202 or 204) could be used to perform one or more of the steps in FIG. 14.

FIG. 15 depicts an illustrative flow diagram 1500 for determining whether the prevention protocol was successful in relation to step 1414 in FIG. 14. At step 1502, the processor receives patient data for determining whether a smoking event occurred. At step 1504, the processor analyzes currently received patient data and previously received patient data. At step 1506, the processor determines whether a smoking event occurred based on the analysis. For example, if no nicotine was administered but the patient's SpCO levels are currently higher than previous SpCO levels, the processor may determine the patient relapsed and smoked a cigarette. In such a situation, at step 1508, the processor returns a message indicating that the prevention protocol was not successful. In another example, if the patient's vital signs indicate no rise or a drop in SpCO levels, the processor may determine that a smoking event did not occur. In such a situation, at step 1510, the processor returns a message indicating that the prevention protocol was successful.

It is contemplated that the steps or descriptions of FIG. 15 may be used with any other embodiment of this disclosure. In addition, the steps and descriptions described in relation to FIG. 15 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 1 (e.g., device 102, 104, or 106) or FIG. 2 (e.g., device 202 or 204) could be used to perform one or more of the steps in FIG. 15.

FIG. 16 depicts an illustrative flow diagram 1600 for a one time measurement of the patient's SpCO level using a PPG sensor. For example, the wearable device, e.g., device 102 or 202, is applied to the patient and receives the sample for a one time measurement of the patient's SpCO level. At step 1602, a processor in the wearable device receives a PPG measurement for the patient's SpCO level and any other suitable data, such as time, location, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. At step 1604, the processor analyzes the received data to determine a recent smoking event. For example, an elevated SpCO level beyond a certain threshold may suggest that the patient has recently smoked a cigarette.

At step 1606, the processor determines whether the patient SpCO level indicates a smoking event has occurred. For example, the SpCO level exceeding a specified threshold may indicate a smoking event. In another example, one or more of shape of the SpCO curve, start point, upstroke, slope, peak, delta, downslope, upslope, time of change, area under curve, and other suitable factors, may indicate a smoking event. One or more of these factors may assist in quantification of the smoking event. For example, the total number of peaks in a given day may indicate the number of cigarettes smoked, while the gradient shape and size and other characteristics of each peak may indicate the intensity and amount of each cigarette smoked. If the processor determines the SpCO level is indicative that a smoking event has not occurred, at step 1608, the processor returns a denial message indicating the patient did not have a recent smoking event. The patient's doctor may find this information useful in evaluating the patient's smoking behavior. If the processor determines the SpCO level is indicative that a smoking event has occurred, at step 1610, the processor returns a confirmation message indicating the patient did have a recent smoking event. In this case, the collected data may be used to set up a quit program for the patient as described above.

After steps 1608 or 1610, at step 1612, the processor updates the patient database to record this information. At step 1614, the processor terminates the SpCO level evaluation for the patient. The patient may be provided with the wearable device to wear as an outpatient for a period of time, e.g., one day, one week, or another suitable period of time. Longer wear times may provide more sensitivity in detection of smoking behavior and more accuracy in quantifying the variables related to smoking behavior.

It is contemplated that the steps or descriptions of FIG. 16 may be used with any other embodiment of this disclosure. In addition, the steps and descriptions described in relation to FIG. 16 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 1 (e.g., device 102, 104, or 106)

or FIG. 2 (e.g., device 202 or 204) could be used to perform one or more of the steps in FIG. 16.

In some embodiments, data from one or more devices associated with patients, such as devices 102 and 104 or device 202, are received at a central location, such as server 106 or 204. The patient devices log in real time or near real time multiple biometric and contextual variables. For example, the biometric variables may include CO, eCO, SpCO, SpO2, heart rate, respiratory rate, blood pressure, body temperature, sweating, heart rate variability, electrical rhythm, pulse velocity, galvanic skin response, pupil size, and other suitable biometric variables. For example, the contextual variables may include GPS location, patient activities (e.g., sports, gym, shopping, or another suitable patient activity), patient environment (e.g., at work, at home, in a car, in a bar, or another suitable patient environment), stressors, life events, and other suitable contextual variables. The collected data may also include in-person observation of the patients' smoking behavior. A spouse or friend or buddy may be able to enter data that their patient smoked, correlating that data with the SpCO readings to determine accuracy.

Server 106 includes a processor for receiving data for multiple patients over a period of time and analyzes the data for trends that occur around the time of an actual smoking event. Based on the trends, the processor determines a diagnostic and/or detection test for a smoking event. The test may include one or more algorithms applied to the data as determined by the processor. For example, the processor may analyze a spike in CO level of a patient. Detecting the spike may include determining that the CO level is above a certain specified level. Detecting the spike may include detecting a relative increase in the patient's CO level from a previously measured baseline. The processor may detect a spike as a change in the slope of the patient's CO trend over a period of time. For example, the CO trend moving from a negative slope to a positive slope may indicate a spike in the CO level. In another example, the processor may apply one or more algorithms to changes in heart rate, increasing heart rate variability, changes in blood pressure, or variation in other suitable data in order to detect a smoking event.

Figure 17:
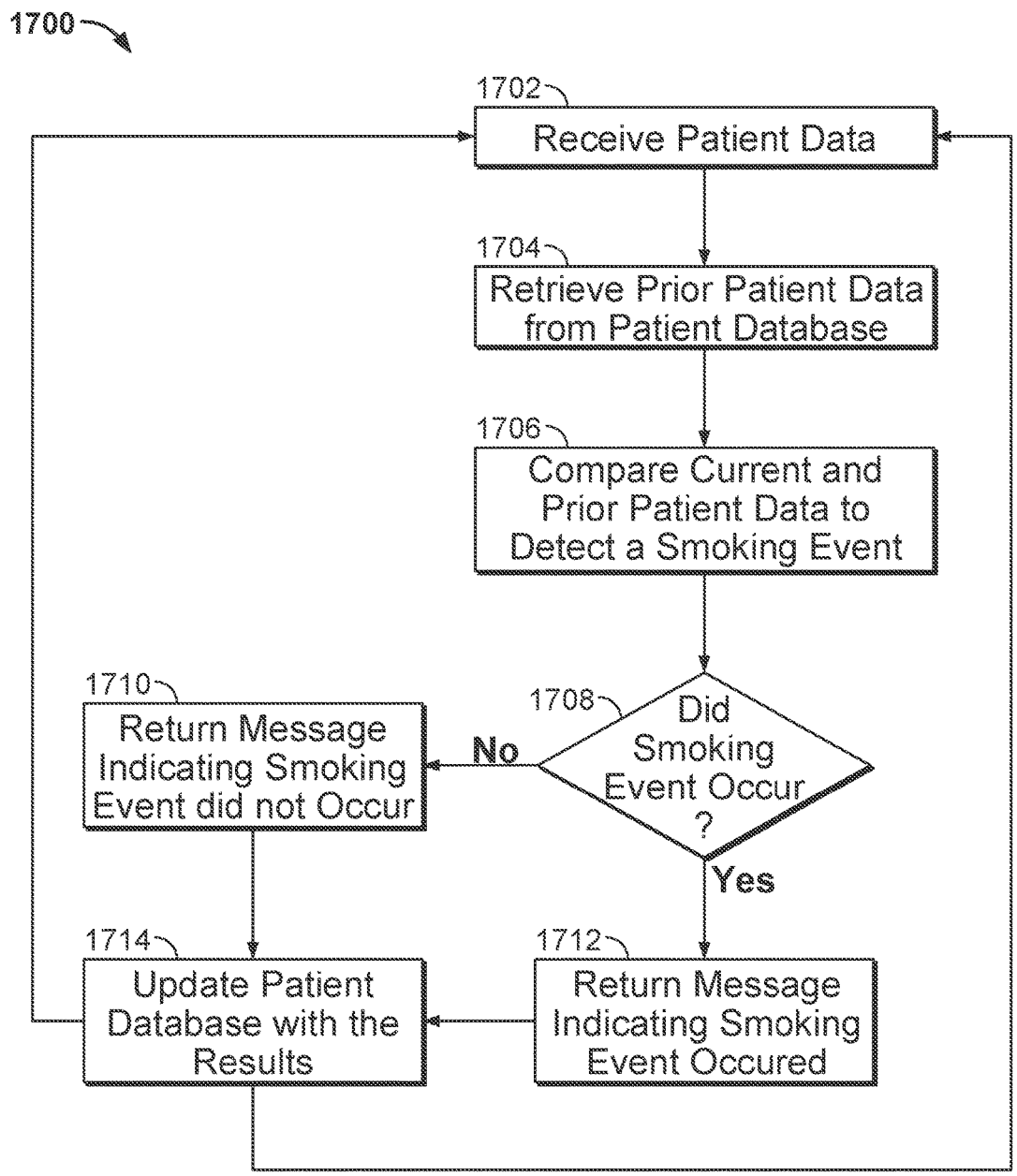
FIG. 17 depicts an illustrative flow diagram for detecting a smoking event in accordance with some embodiments of the disclosure.

FIG. 17 depicts an illustrative flow diagram 1700 for detecting a smoking event as described above. A processor (e.g., in server 106 or 204) may determine a diagnostic and/or detection test for a smoking event according to flow diagram 1700. At step 1702, the processor receives current patient data. At step 1704, the processor retrieves previously stored data for the patient from a database, e.g., a patient database stored at server 106 or 204. At step 1706, the processor compares the current and prior patient data to detect a smoking event. For example, the processor may analyze a spike in CO level of the patient. Detecting the spike may include detecting a relative increase in the patient's CO level from a previously measured baseline. The processor may detect a spike as a change in the slope of the patient's CO trend over a period of time. For example, the CO trend moving from a negative slope to a positive slope may indicate smoking behavior. In another example, the processor may apply one or more algorithms to changes in heart rate, increasing heart rate variability, changes in blood pressure, or variation in other suitable data in order to detect a smoking event. At step 1708, the processor determines whether a smoking event occurred based on, e.g., a spike in CO level of the patient as described. If no smoking event is detected, at step 1710, the processor returns a message indicating that smoking event did not occur. If a smoking event is detected, at step 1712, the processor returns a message indicating that a smoking event occurred. At step 1714, the processor updates the patient database with the results from either step 1710 or 1712.

It is contemplated that the steps or descriptions of FIG. 17 may be used with any other embodiment of this disclosure. In addition, the steps and descriptions described in relation to FIG. 17 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 1 (e.g., device 102, 104, or 106) or FIG. 2 (e.g., device 202 or 204) could be used to perform one or more of the steps in FIG. 17.

In some embodiments, the processor analyzes initially received data to measure when a person smokes and ties the algorithm to a variable that triggers the algorithm for diagnosing and/or detecting a smoking event. The processor continues to analyze other variables as additional patient data is received. The processor may determine another variable that changes when the patient smokes and instead use that variable to trigger the algorithm. For example, the processor may opt to use the other variable because it is less invasive or easier to measure than the initially selected variable.

In some embodiments, the algorithm for detecting a smoking event has a high sensitivity. Sensitivity is defined as a percentage of the number actual smoking events detected by the sensor and algorithm. For example, if a patient smokes 20 times in one day, and the algorithm identifies every smoking event, it is 100% sensitive.

In some embodiments, the algorithm for detecting a smoking event has a high specificity. Specificity is defined as the ability of the test to not make false positive calls of a smoking event (i.e., positive test with no smoking event present). If the sensor and algorithm do not make any false positive calls in a day, it has 100% specificity.

In another example, if a patient smokes 20 times and the algorithm identifies 18 of the 20 actual smoking events and indicates 20 other false smoking events, it has 90% sensitivity (i.e., detected 90% of smoking events) and 50% specificity (i.e., over called the number of smoking events by 2×).

In some embodiments, after the processor determines one or more algorithms and applies to SpCO measurements to detect a smoking event with adequate sensitivity and specificity, the processor determines whether there is an association of other biometric variables or contextual variables with the SpCO results that could be used on their own (without SpCO) to detect a smoking event. The processor may determine another variable that changes when the patient smokes and instead use that variable to trigger the algorithm. For example, the processor may opt to use the other variable because it is less invasive or easier to measure or more reliable than the initially selected variable.

In some embodiments, the processor analyzes received patient data to predict a smoking event likelihood before it happens. The processor may analyze received patient data over a period of time, e.g., five minutes, 10 minutes, 15 minutes, 20 minutes, or another suitable time interval, before a smoking event to determine one or more triggers. For example, some smoking events may be preceded by contextual triggers (e.g., at a bar, before, during, or after eating, before, during, or after sex, or another suitable contextual trigger). In another example, some smoking events may be preceded by changes in a biometric variable, e.g., heart rate or another suitable biometric variable. The determined variables may overlap with those selected for diagnosis and detection and therefore may be used for prediction as well. Alternatively, the determined variables may not overlap with those selected for diagnosis.

The processor may inform patients of a smoking event likelihood and trigger a prevention protocol (e.g., as discussed with respect to FIGS. 14 and 15) to prevent smoking change behavior. The processor detects smoking events for a patient entered in, e.g., a quit program, and tracks and analyses trends in received patient data. The processor may determine goals for the patient and reward them when he achieves the set goals (e.g., as discussed with respect to FIG. 13). The processor may predict when a patient is about to smoke and intervene just in time by suggesting a call to a peer group or a physician or by administering a bolus of nicotine (e.g., as discussed with respect to FIG. 12).

In one example, the processor predicts smoking events for the patient based on 75% of the patient's smoking events, during diagnosis, being preceded by increased heart rate (or a suitable change in another variable). During the quit program, the processor may apply one or more algorithms to received patient data to predict smoking events and initiate a prevention protocol. For example, the prevention protocol may engage the patient just in time by putting the patient in contact with supporters, such as a doctor, a counselor, a peer, a team member, a nurse, a spouse, a friend, a robot, or another suitable supporter. In some embodiments, the processor applies algorithms to adjust settings, such as baseline, thresholds, sensitivity, and other suitable settings, for each patient based on their five-day run-in diagnostic period. The processor may then use these customized algorithms for the specific patient's quit program. The described combination of techniques to alter smoking behavior in a patient may be referred to as a digital drug.

In some embodiments, the processor detects smoking in a binary manner with a positive or a negative indication. The processor initially uses observational studies and SpCO measurements from the patient to detect smoking behavior. For example, the processor receives data regarding true positives for smoking events from observational data for the patient's smoking behavior. The processor determines if detection based on SpCO measurements matches true positives for smoking events. If there is a match, the processor applies algorithms to other received patient data including patient's SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. The processor determines whether any patterns in non-SpCO variable data are also indicative of a smoking event. Such variables may be used in algorithms for non-SpCO devices, such as wearable smart watches or heart rate monitor straps or other devices, to detect smoking events.

The processor may quantify smoking behavior when it is detected based on the received patient data. For example, the processor analyzes SpCO data trends to indicate how intensely the patient smoked each cigarette, how many cigarettes the patient smoked in one day, how much of each cigarette was smoked, and/or how long it took to smoke each cigarette. The processor may use other biometric or contextual variables for the indications as well. The processor uses the received patient data to predict the likelihood for a smoking event to occur in the near future, e.g., in the next 10 minutes. The processor may analyze the received patient data over a preceding period of time, e.g., five minutes, 10 minutes, 15 minutes, 20 minutes, or another suitable time interval, before a smoking event to determine one or more triggers.

In some embodiments, the systems and methods described herein provide for evaluating smoking behavior of a patient. During a five-day testing period, the patient behaves as they normally would. Devices 102, 104, and/or 106 or devices 202 and/or server 204 receive patient data relating to the patient's smoking behavior. There is very little to no engagement of the patient as the purpose of the testing period is to observe the patient's smoking patterns. The testing period may be extended to a second five-day period if needed. Alternatively, the first and second periods may be shorter, e.g., two or three days, or longer, e.g., a week or more. Before the second testing period, the processor determines a model of how the patient smokes.

In the second testing phase, the processor applies a series of perturbations to the model to see if the smoking behavior changes. There may be several types of perturbations, each with several dimensions. For example, the perturbation may be whether sending a text message before or during a smoking event causes the smoking event to be averted or shortened. Dimensions within the perturbation may be different senders, different timing, and/or different content for the text messages. In another example, the perturbation may be whether a phone call at certain times of the day or before or during a smoking event causes the smoking event to be averted or shortened. Dimensions within the perturbation may be different callers, different timing, and/or different content for the phone calls. In yet another example, the perturbation may be whether alerting the patient to review their smoking behavior at several points in the day averts smoking for a period of time thereafter. Dimensions may include determining whether and when that aversion extinguishes. In other examples, the perturbations may be rewards, team play, or other suitable triggers to avert or shorten the patient's smoking events.

In some embodiments, the processor delivers perturbations to the smoking model for the patient using a machine learning process. The machine learning process delivers perturbations, tests the results, and adjusts the perturbation accordingly. The processor determines what works best to achieve an identified behavior change by trying options via the machine learning process. The machine learning process may be applied during the second testing phase as slight perturbations. The machine learning process may be also be applied with significant perturbations during the patient's quit phase to increase efforts to try to get the patient to quit smoking or to continue to abstain from smoking.

Figure 18:
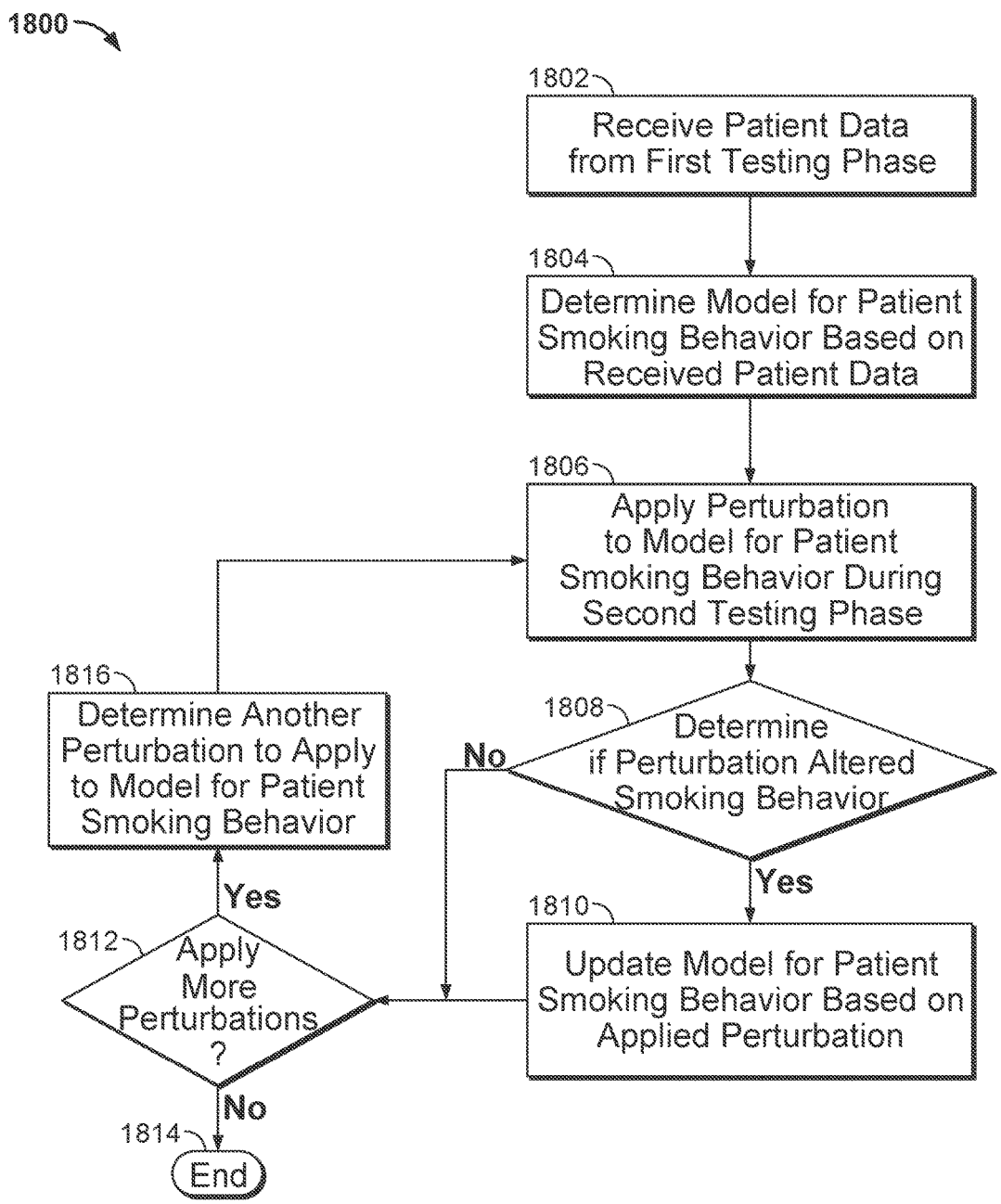
FIG. 18 depicts an illustrative flow diagram for applying one or more perturbations to a model for a patient's smoking behavior in accordance with some embodiments of the disclosure.

FIG. 18 depicts an illustrative flow diagram 1800 for applying one or more perturbations to the smoking model for the patient in the second testing phase. At step 1802, a processor in wearable device 102 or 202, mobile device 104, or server 106 or 204 receives patient data relating to the patient's smoking behavior in the first testing phase. At step 1804, the processor analyzes the received patient data to determine a model for the patient's smoking behavior. At step 1806, the processor applies one or more perturbations to the model to see if the smoking behavior changes. The perturbation may be applied to the model using a machine learning process. There may be several types of perturbations, each with several dimensions. For example, the perturbation may be whether sending a text message before or during a smoking event causes the smoking event to be averted or shortened. Dimensions within the perturbation may be different senders, different timing, and/or different content for the text messages.

At step 1808, the processor determines whether the perturbation altered the patient's smoking behavior. For example, the processor determines whether receiving a text message before or during a smoking event caused the patient to abstain from or shorten his smoking. If the perturbation caused a change in the patient's smoking behavior, at step 1810, the processor updates the model for the patient's smoking behavior to reflect the positive result of the applied perturbation. The processor then proceeds to step 1812. Otherwise, the processor proceeds directly to step 1812 from step 1808 and determines whether to apply another perturbation or a variation in the dimensions of the present perturbation. The processor may use the machine learning process to determine whether to apply additional perturbations to the model. If no more perturbations need to be applied, at step 1814, the processor ends the process of applying perturbations.

If more perturbations need to be applied, at step 1816, the processor determines another perturbation to apply to the model. For example, the processor may adjust the present perturbation to send a text message to the patient at a different time or with different content. In another example, the processor may apply a different perturbation by initiating a phone call to the patient before or during a smoking event. The processor returns to step 1806 to apply the perturbation to the model. The processor may use the machine learning process to deliver a perturbation, test the result, and adjust the perturbation or selected another perturbation accordingly. In this manner, the processor determines what works best to achieve an identified behavior change for the patient by trying different options via the machine learning process.

It is contemplated that the steps or descriptions of FIG. 18 may be used with any other embodiment of this disclosure. In addition, the steps and descriptions described in relation to FIG. 18 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 1 (e.g., device 102, 104, or 106) or FIG. 2 (e.g., device 202 or 204) could be used to perform one or more of the steps in FIG. 18.

In an illustrative example, a 52-year old male patient is incentivized by his employer to get screened for smoking behavior. The patient enters an evaluation program on Jun. 1, 2015. The patient reports smoking 20 cigarettes per day. The program coordinator, such as a physician or counselor, loads an app on the patient's smart phone, e.g., mobile device 104, and gives the patient a connected sensor, e.g., wearable device 102 or 202. The coordinator informs the patient to smoke and behave normally for a five-day testing period and respond to prompts from the app as they arise. After the five-day period is over, the coordinator enters the patient into a supplementary testing period where the app prompts a bit more often (e.g., to apply perturbations). The coordinator informs the patient that it is up to him at that point to respond however he wishes. The coordinator establishes a targeted date of Jun. 10, 2015 to include 10 days of testing.

After the five-day testing period, the coordinator receives a report (e.g., a five-day report card as discussed with respect to FIG. 8). The report indicates 150 cigarette smoking events detected using CO as compared to 100 cigarette smoking events based on the patient's estimate. The report indicates that associated contextual variables include alcohol, location, stress, and other suitable data. The report indicates that associated biometric variables include increased heart rate, without exercise, as preceding 50% of smoking events. The report indicates that prompts for stress levels showed increased stress in 20% of smoking events.

During the supplementary five-day test period, a processor in the mobile device, e.g., device 104, the wearable device, e.g., device 102 or 202, or a remote server, e.g., server 106 or 204, applies perturbations via a machine learning process. For example, the mobile device prompts the patient four time times a day with a display including number of cigarettes smoked, intensity of smoking, and time of day. As the day progresses, the prompts cause the patient to reduce smoking for longer periods of time. The net effect is that the patient smokes fewer cigarettes in the second half of day as compared to the first half. In another example, the mobile device prompts the patient at 10 am everyday with a display including number of cigarettes smoked the previous day. The net effect is studied as to how the prompt impacts the patient's smoking behavior for the rest of day. The machine learning process may adjust time and content of the display to alter the dimensions of the perturbation as required.

In another example, the processor applies a perturbation via a machine learning process in the form of a text message sent to the patient during a smoking event. The machine learning process varies the dimensions of the perturbation by having different senders, different timing, sending before or during smoking, different content of message, different images in the message, and/or different rewards for abstaining. In another example, the processor applies a perturbation via a machine learning process in the form of a phone call to the patient during a smoking event. The machine learning process varies the dimensions of the perturbation by having different callers, different timing, calling before or during smoking, different content of call, different tones in the call, and/or different rewards for abstaining.

In another example, the processor applies a perturbation via a machine learning process in the form of a prompt for a particular activity on the patient's mobile device. The prompt indicates that the patient is smoking but should consider smoking only half a cigarette and then get outside. During long times between cigarette events, or when an event is predicted, the machine learning process applies perturbations to attempt to avert the smoking event completely. For example, the mobile device displays a prompt notifying the patient that they are in a high risk zone and should consider an alternative activity or location or phone a friend.

After the testing period, the coordinator enters the patient into the quit program. During the quit period, the processor receives patient data and applies algorithms to the data as described. The processor uses all data from the first and second testing periods to customize the algorithms and starting regimen and quit program interventions for the specific patient. The diagnostic and detection algorithms may use one or more biometric variables for the patient, such as SpCO, to detect smoking behavior. The quit program includes a nicotine regimen starting on day one as part of the nicotine replacement therapy. The nicotine may be delivered via a transdermal patch or a transdermal transfer from a reservoir of nicotine stored in the wearable device given to the patient. The processor applies algorithms to the received patient data to determine the most effective interventions. The processor applies the interventions and further adjusts them as required. The processor may set goal event counts and determine which method works best for altering the patient's smoking behavior. The processor may invoke multiple personalized interventions from stakeholders as perturbations via the machine learning process and test which works best for altering the patient's smoking behavior. The perturbations with the most impact on the patient's smoking model may be retained, while those with less or no impact may not be used further.

While exemplary embodiments of the systems and methods described above focus on smoking behaviors, examples of which include but are not limited to smoking of tobacco via cigarettes, pipes, cigars, and water pipes, and smoking of illegal products such as marijuana, cocaine, heroin, and alcohol related behaviors, it will be immediately apparent to those skilled in the art that the teachings of the present invention are equally applicable to any number of other undesired behaviors. Such other examples include: oral placement of certain substances, with specific examples including but not limited to placing chewing tobacco and snuff in the oral cavity, transdermal absorption of certain substances, with specific examples including but not limited to application on the skin of certain creams, ointments, gels, patches or other products that contain drugs of abuse, such as narcotics, and LSD, and nasal sniffing of drugs or substances of abuse, which includes but is not limited to sniffing cocaine.

In general, the basic configuration of devices 102 and 104 or device 202, as well as related steps and methods as disclosed herein will be similar as between the different behaviors that are being addressed. The devices may differ somewhat in design to account for different target substances that are required for testing or different testing methodology necessitated by the different markers associated with particular undesired behaviors.

It will also be appreciated by persons of ordinary skill in the art that a patient participating in a formal cessation program may take advantage of the systems and methods disclosed herein as adjuncts to the cessation program. It will be equally appreciated that the patient may be independently self-motivated and thus beneficially utilize the systems and methods for quitting the undesired behavior unilaterally, outside of a formal cessation program.

In further exemplary embodiments, the systems and methods disclosed herein may be readily adapted to data collection and in particular to collection of reliable and verifiable data for studies related to undesired behaviors for which the present invention is well suited to test. Such studies may be accomplished with virtually no modification to the underlying device or methods except that where treatment was not included there would not necessarily be a need for updating of the test protocol or treatment protocol based on user inputs.

Figure 19:
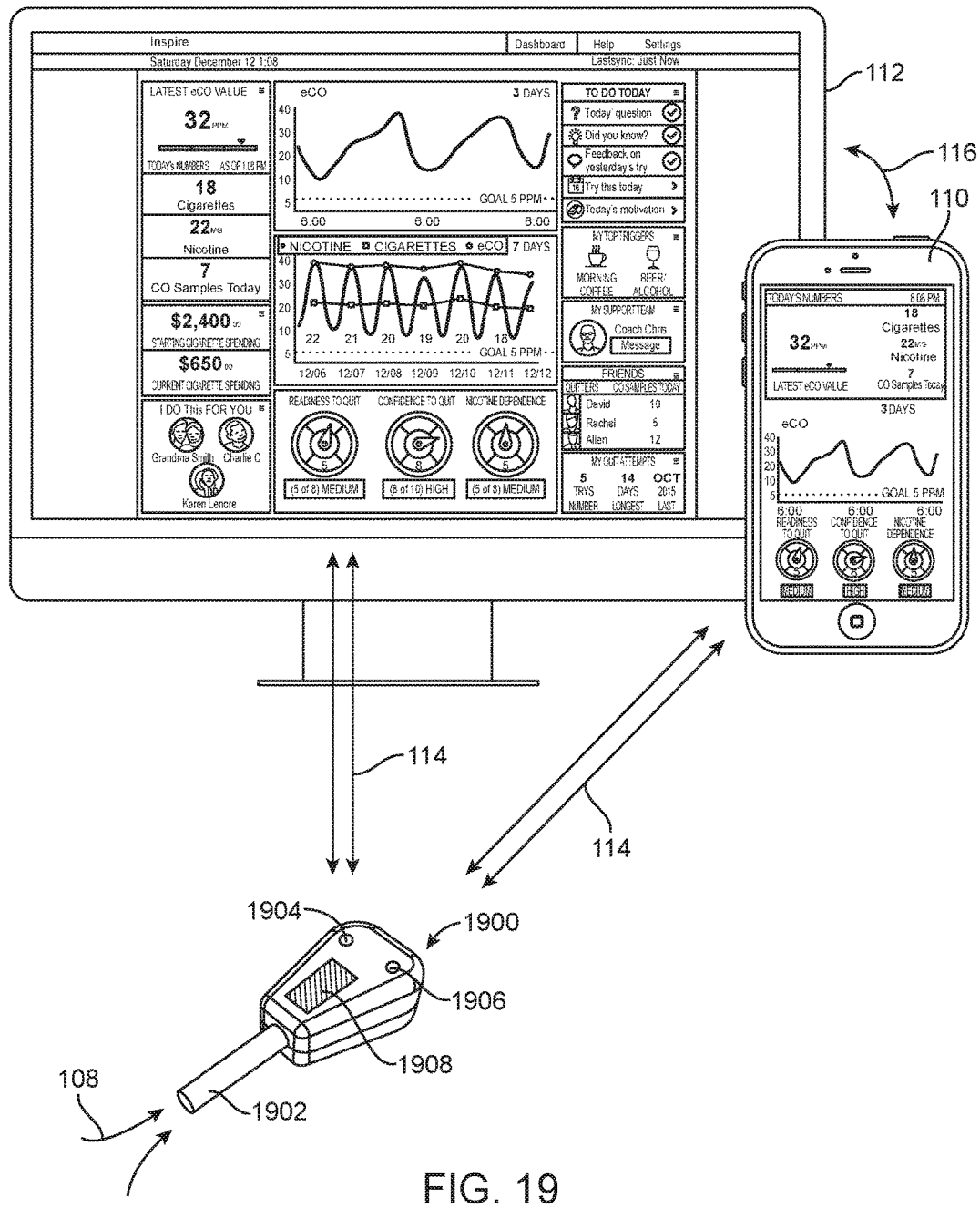
FIG. 19 illustrates another variation of a system and/or method for affecting an individual's smoking behavior using a number of the aspects described herein as well as further quantifying an exposure of the individual to cigarette smoke.

FIG. 19 illustrates another variation of a system and/or method for affecting an individual's smoking behavior using a number of the aspects described herein as well as further quantifying an exposure of the individual to cigarette smoke. In the illustrated example, a plurality of samples of biometric data are obtained from the individual and analyzed to quantify the individual's exposure to cigarette smoke such that the quantified information can be relayed to the individual, a medical caregiver, and/or other parties having a stake in the individual's health. The example discussed below employs a portable device 1900 that obtains a plurality of samples of exhaled air from the individual with commonly available sensors that measure an amount of carbon monoxide within the sample of exhaled air (also referred to as exhaled carbon monoxide or ECO). However, the quantification and information transfer is not limited to exposure of smoking based on exhaled air. As noted above, there are many sampling means to obtain an individual's smoking exposure. The methods and devices described in the present example can be combined or supplemented with such sampling means where possible while still remaining with the scope of the invention. In addition, while the present example discusses the use of a portable sampling unit, the methods and procedures described herein can be used with a dedicated or non-portable sampling unit.

The measurement of exhaled CO level has been known to serve as an immediate, non-invasive method of assessing a smoking status of an individual. See for example, *The Measurement of Exhaled Carbon Monoxide in Healthy Smokers and Non-smokers*, S. Erhan Devecia, et al., Department of Public Health, Medical Faculty of Firat University, Elazig, Turkey 2003 and *Comparison of Tests Used to Distinguish Smokers from Nonsmokers*, M. J. Jarvis et al. American Journal of Public Health, November 1987, V77, No. 11. These articles discuss that exhaled CO ("eCO") levels for non-smokers can range between 3.61 ppm and 5.6 ppm. In one example, the cutoff level for eCO was above 8-10 ppm to identify a smoker.

Turning back to FIG. 19, as shown a portable or personal sampling unit 1900 communicates with either a personal electronic device 110 or a computer 112. Where the personal electronic device 110 includes, but is not limited to a smart phone, ordinary phone, cellular phone, or other personal transmitting device exclusively designed for receiving data from the personal sampling unit 1900). Likewise, the computer 112 is intended to include a personal computer, local server, or a remote server. Data transmission 114 from the personal sampling unit 1900 can occur to both or either the personal electronic device 110 and/or the computer 112. Furthermore, synchronization 116 between the personal electronic device 110 and the computer 112 is optional. Either the personal electronic device 110, the computer 112, and/or the personal sampling unit 1900 can transmit data to a remote server for data analysis as described herein. Alternatively, data analysis can occur, fully or partially, in a local device (such as the computer or personal electronic device). In any case, the personal electronic device 100 and/or computer 112 can provide information to the individual, caretaker, or other individual as shown in FIG. 19.

In the depicted example of FIG. 19, the personal sampling unit 1900 receives a sample of exhaled air 108 from the individual via a collection tube 1902. Hardware within the personal sampling unit 1900 includes any commercially available electrochemical gas sensor that detects carbon monoxide (CO) gas within the breath sample, commercially available transmission hardware that transmits data 114 (e.g., via Bluetooth, cellular, or other radio waves to provide transmission of data). The transmitted data and associated measurements and quantification are then displayed on either (or both) a computer display 112 or a personal electronic device 110. Alternatively, or in combination, any of the information can be selectively displayed on the portable sampling unit 1900.

The personal sampling unit (or personal breathing unit) can also employ standard ports to allow direct-wired communication with the respective devices 110 and 112. In certain variations, the personal sampling unit 1900 can also include memory storage, either detachable or built-in, such the memory permits recording of data and separate transmission of data. Alternatively, the personal sampling unit can allow simultaneous storage and transmission of data. Additional variations of the device 1900 do not require memory storage. In addition, the unit 1900 can employ any number of GPS components, inertial sensors (to track movement), and/or other sensors that provide additional information regarding the patient's behavior.

The personal sampling unit 1900 can also include any number of input trigger (such as a switch or sensors) 1904, 1906. As described below, the input trigger 1904, 1906 allow the individual to prime the device 1900 for delivery of a breath sample 108 or to record other information regarding the cigarette such as quantity of cigarette smoked, the intensity, etc. In addition, variations of the personal sampling unit 1900 also associate a timestamp of any inputs to the device 1900. For example, the personal sampling unit 1900 can associate the time at which the sample is provided and provide the measured or inputted data along with the time of the measurement when transmitting data 114. Alternatively, the personal sampling device 1900 can use alternate means to identify the time that the sample is obtained. For example, given a series of samples rather than recording a timestamp for each sample, the time periods between each of the samples in the series can be recorded. Therefore, identification of a timestamp of any one sample allows determination of the time stamp for each of the samples in the series.

In certain variations, the personal sampling unit 1900 is designed such that it has a minimal profile and can be easily carried by the individual with minimal effort. Therefore the input triggers 1904 can comprise low profile tactile switches, optical switches, capacitive touch switches, or any commonly used switch or sensor. The portable sampling unit 1900 can also provide feedback or information to the user using any number of commonly known techniques. For example, as shown, the portable sampling unit 1900 can include a screen 1908 that shows select information as discussed below. Alternatively or in addition, the feedback can be in the form of a vibrational element, an audible element, and a visual element (e.g., an illumination source of one or more colors). Any of the feedback components can be configured to provide an alarm to the individual, which can serve as a reminder to provide a sample and/or to provide feedback related to the measurement of smoking behavior. In addition, the feedback components can provide an alert to the individual on a repeating basis in an effort to remind the individual to provide periodic samples of exhaled air to extend the period of time for which the system captures biometric (such as eCO, CO levels, etc.) and other behavioral data (such as location either entered manually or via a GPS component coupled to the unit, number of cigarettes, or other triggers). In certain cases, the reminders can be triggered at higher frequency during the initial program or data capture. Once sufficient data is obtained, the reminder frequency can be reduced.

Figure 20A:
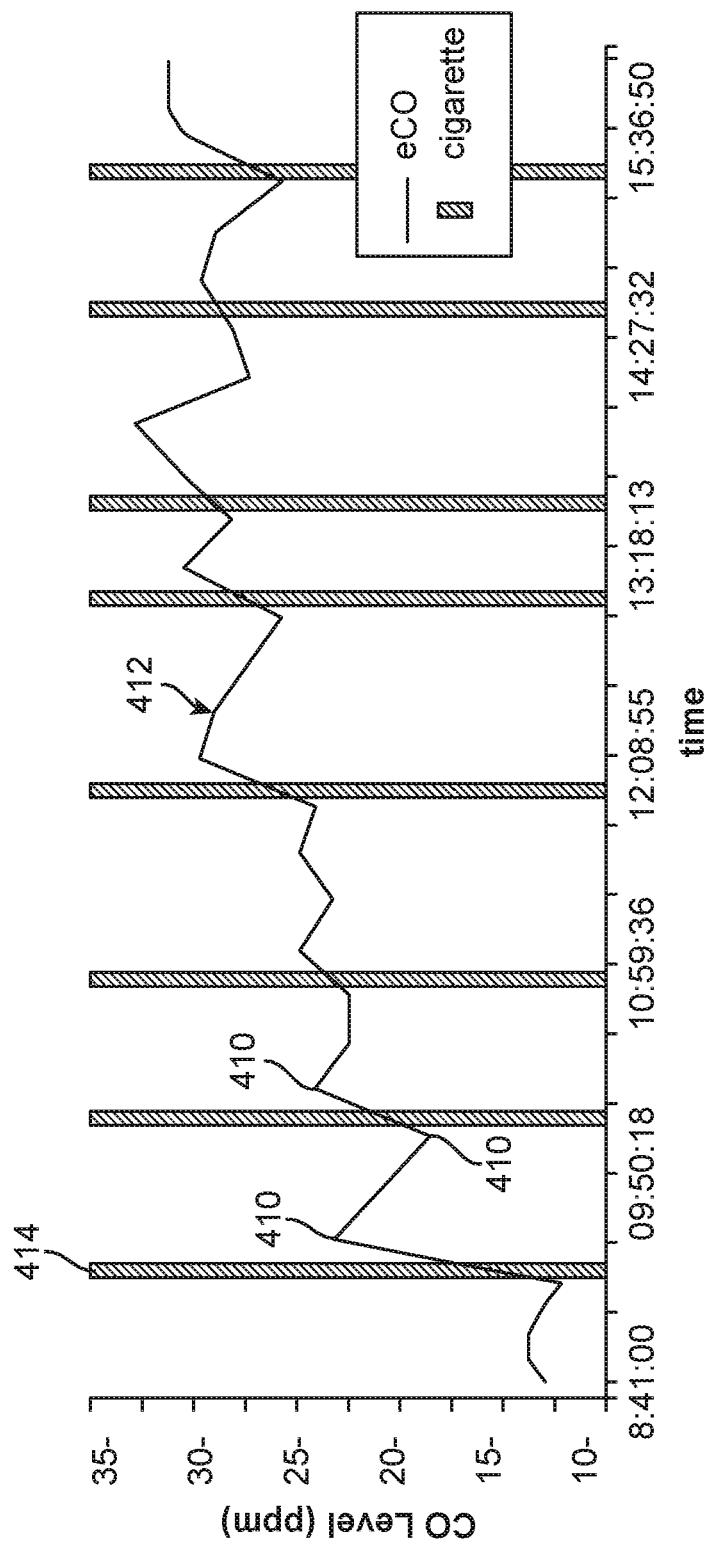
FIG. 20A illustrates a visual representation of data that can be collected with variations of the system shown in FIG. 19.

FIG. 20A illustrates a visual representation of data that can be collected with variations of the system shown in FIG. 19. As discussed above, an individual provides breath samples using the portable sampling unit. The individual can be reminded at a regular interval or at random intervals depending upon the nature of the treatment or intervention program. Each sample is evaluated by one or more sensors within the portable sampling unit to measure an amount of CO. The CO measurements typically correspond to the inflection points 410 on the graph of FIG. 20A. Each CO measurement 410 corresponds to a timestamp as shown in the horizontal axis. The data accumulated via the portable sampling unit allows for the collection of a dataset comprising at least the CO measurement and time of the sample which can be graphed to obtain an eCO curve which is indicative of the amount of CO attributable to the smoking behavior of the individual over the course of the time period.

As noted herein, the individual can further track additional information such as smoking of a cigarette. The smoking of the cigarette can be associated with its own time stamp as shown by bar 414. In one variation of the method and system under the present disclosure, the individual can use the input triggers on the portable sampling unit to enter the number of cigarettes smoked or a fraction thereof. For example, each actuation of the input trigger can be associated with a fractional amount of a cigarette (e.g., ½, ⅓, ¼, etc).

Figure 20B:
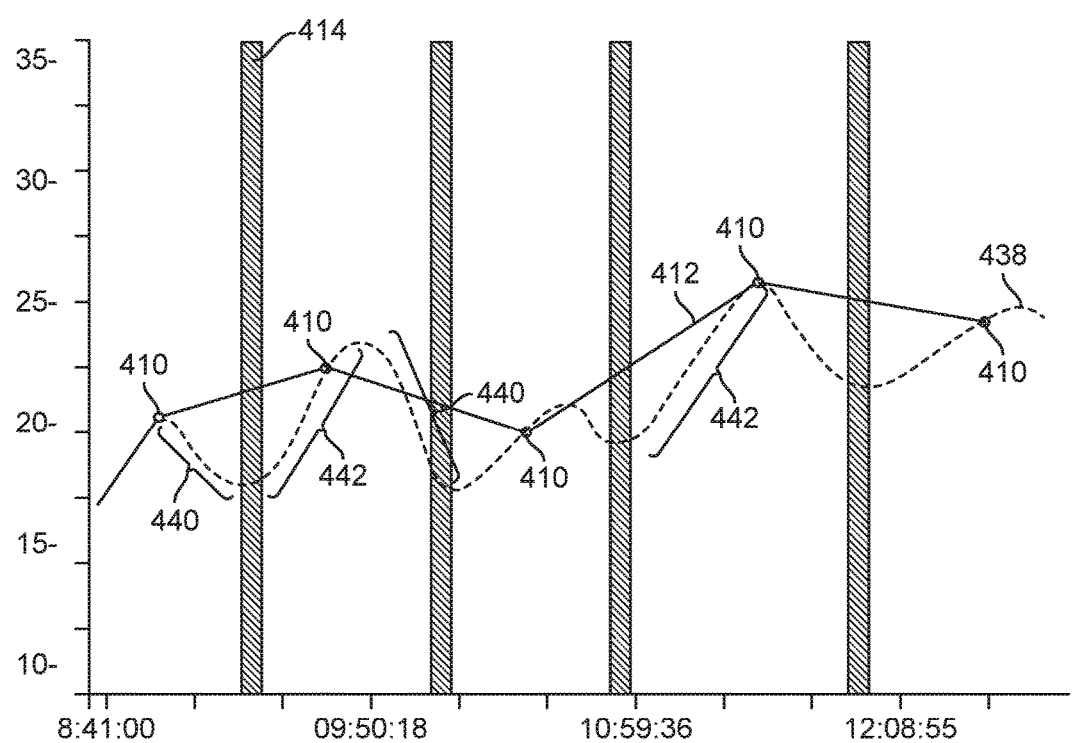
FIG. 20B illustrates a visual representation of data that can be collected with variations of the system shown in FIG. 19.

FIG. 20B illustrates a portion of a graphic representation of data collected as described above. However, in this variation, the quantification of an individual's smoking behavior can use behavioral data to better approximate the CO value between eCO readings. For example, in some variations, eCO measurements between any two points 410 can be approximated using a linear approximation between the two points. However, it is known that, in the absence of being exposed to new CO, the CO level decay within the bloodstream. This decay can be approximated using a standard rate, a rate based on the biometric information of the patient (weight, heartbeat, activity, etc.) As shown in FIG. 20B, when the patient is between cigarettes 414, the calculated CO level can follow a decay rate 440. Once the individual records a cigarette 414, the CO increase 442 can again be approximated, either by using a standard rate or one that is calculated using biometric data as discussed above, or based on the intensity, duration, and amount of cigarettes smoked. Accordingly, the methods and system described herein can optionally use an improved (or approximated) eCO curve 438 using the behavioral data discussed above. Such an improved eCO rate can also be used to determine an improved eCO curve 438 while the individual sleeps. This improved eCO curve can then provide an improved eCO load as described herein. The biometric information used to determine decay rate can be measured by the portable sampling device or by external biometric measuring devices that communicate with the system.

This approximated or improved eCO curve 438 can be displayed to the individual (or to a third party) as a means to help change behavior as the individual can view a real time approximated CO level (i.e., the rate of decrease when not smoking and the rate of increase when smoking). Additional information can also be displayed, for example, the system can also calculate the amount of CO increase with each cigarette based on their starting CO value.

Figure 21:
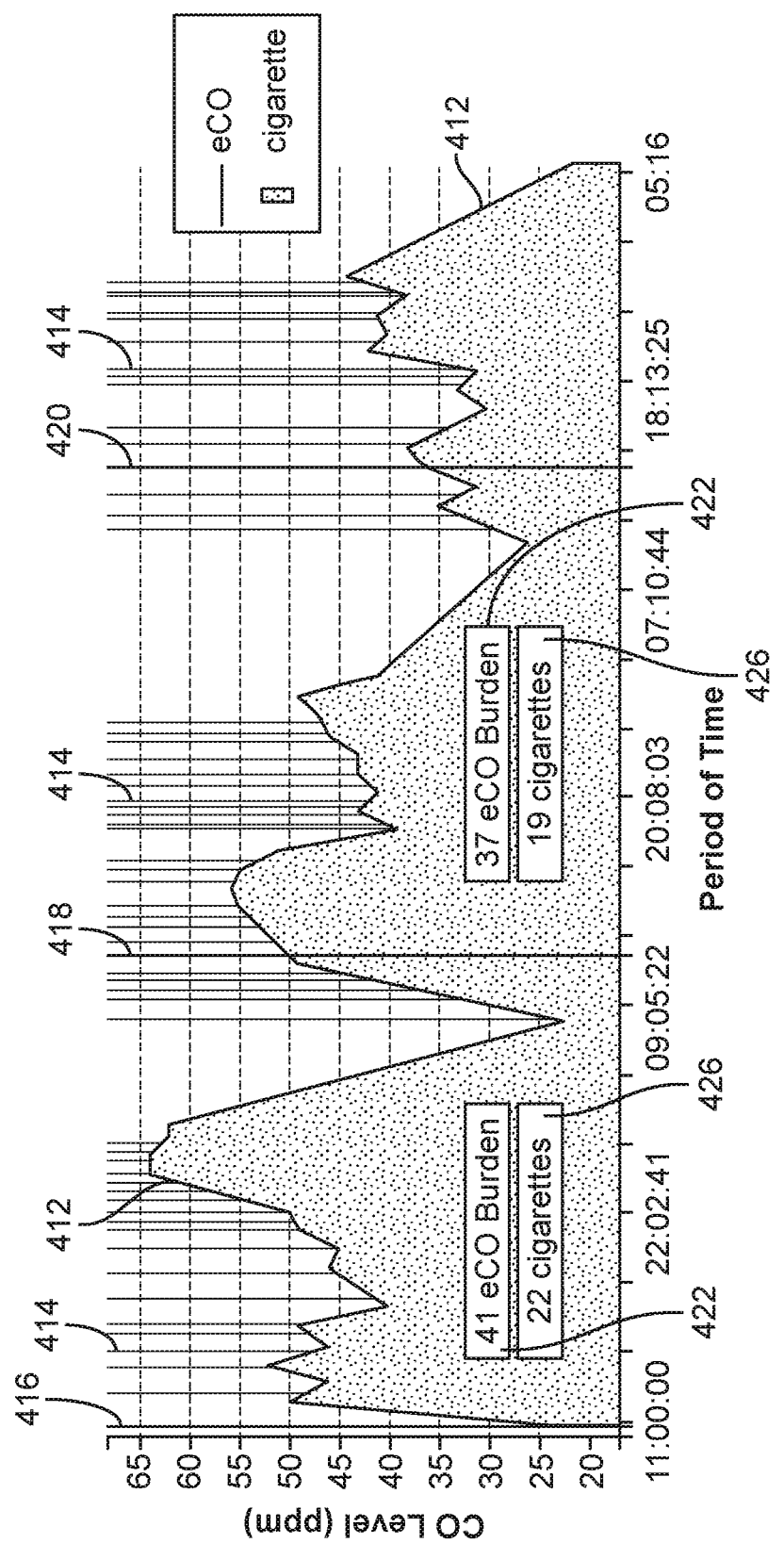
FIG. 21 illustrates an example of a dataset used to determine the eCO curve over a period of time where the eCO attributable to the smoking behavior of the individual can be quantified over various intervals of time to determine an eCO Burden or eCO Load for each interval.

FIG. 21 illustrates an example of a dataset used to determine the eCO curve 412 over a period of time where the eCO attributable to the smoking behavior of the individual can be quantified over various intervals of time to determine an eCO Burden or eCO Load for each interval. As shown, the period of time extends along the horizontal axis and comprises historical and ongoing data captured/transmitted by the portable sampling unit. In order to provide more effective feedback to the individual regarding their smoking behavior, the eCO curve 412 during a certain time interval can be quantified. In the illustrated example, the interval of time between times 416 and 418 comprises a 24 hour interval of time. A subsequent 24 hour interval is defined between times 418 and 420. The interval of time or time interval can comprise any time between two points within the period of time spanned by the dataset. In most cases, the interval of time will be compared to other intervals of time having the same time duration (i.e., where each interval can comprise M minutes, H hours, D days, etc.).

One way of quantifying the eCO Burden/Load over the interval of time is to obtain the area defined by or underneath the eCO curve 412 between a given interval of time (e.g., 416 to 418, 418 to 420, etc.) using the dataset as shown in the graph of FIG. 21. In the illustrated example, the eCO Burden/Load 422 for the first interval (416 to 418) comprises 41 (measured in COppm*t), while the eCO Burden 422 for the second interval (418 to 420) comprises 37. As noted above, along with the eCO Burden/Load 422, the dataset can include the number of cigarettes smoked 414 along with the timestamp of each cigarette. This cigarette data can also be summarized 426 along with the eCO Burden/Load 422 for any given interval of time. In the illustrated example, the eCO Burden/Load is a daily load, which allows the individual to track their CO exposure. Determining a CO Load is a more accurate reflection of total smoke exposure compared to simply counting cigarettes because smokers smoke differently. One smoker may smoke the entire cigarette fully and deeply and intensely, while another smokes less deeply and intensely. While both individuals may smoke one pack per day, the former will have a much higher Daily CO Load due to the intensity that the smoke is inhaled. CO Load is also important as when an individual becomes a patient in a quit-smoking program. In such a case, the quantification allows a caregiver or counselor to follow the patient along during as the patient reduces their smoking activity. For example, the patient may reduce from 20 cigs per day to 18 to 16 and so on. However, at 10 cigs per day, the patient may still have a Daily CO Load that has not lowered because they are compensating when the smoke the reduced number of cigarette (i.e., the patient smokes harder and deeper and more intensely). The patient's reduced smoking exposure only occurs when their CO load decreases.

The data shown in FIG. 21 is intended for illustration purposes only and the duration of the period of time for a given dataset depends on the amount of time the individual uses the portable sampling unit to capture the biometric and behavioral data. Quantifying the exposure of exhaled carbon monoxide comprises correlating a function of exhaled carbon monoxide versus time over the period of time using the dataset and obtaining the area under the eCO curve 412. In variations of the method and system, the eCO curve can be calculated or approximated.

Figure 22:
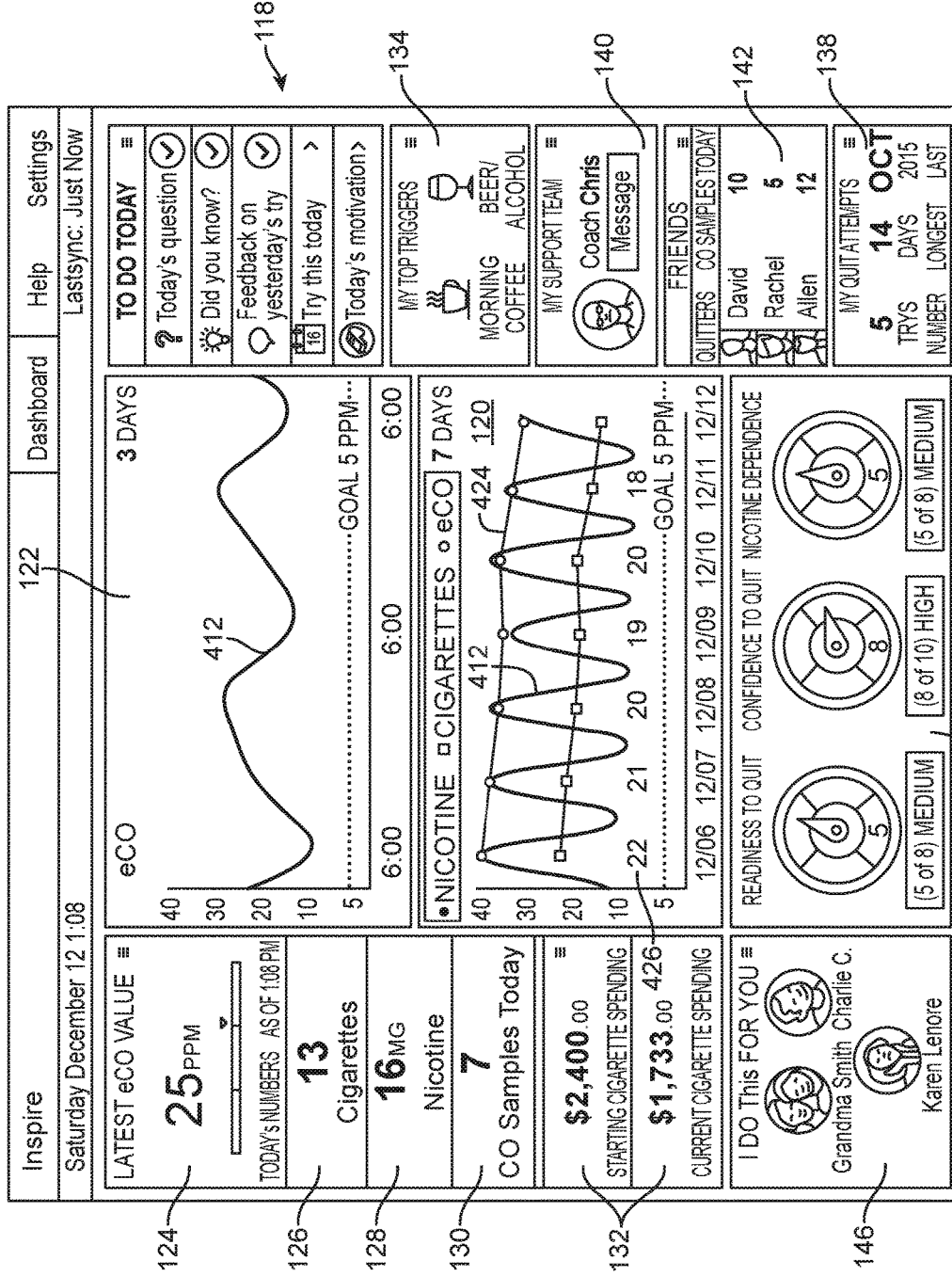
FIG. 22 illustrates an example of displaying the biometric data as well as various other information for assessing the smoking behavior of the individual.

FIG. 22 illustrates an example of displaying the biometric data as well as various other information for the benefit of the user, caregiver, or other party having an interest in assessing the smoking behavior of the individual. The data illustrated in FIG. 22 is for purposes of illustration and can be displayed on the portable electronic device (e.g., see 110 in FIG. 19) or on one or more computers. In addition, any of the biometric data or other data can be displayed on the portable sampling unit 1900.

FIG. 22 illustrates a "dashboard" view 118 of the individual's smoking behavioral data including a graphical output 120 of the eCO curve 412 over a period of time as well as the cigarette count for any given interval of time within the period of time. Graphical output 120 can also provide a measured or calculated nicotine trend 424. This nicotine trend 424 can be determined from the number of cigarettes smoked 426 rather than being a direct measurement of nicotine.

FIG. 22 also illustrates a second graphical output display 122 of an eCO curve 412 over an alternate time period. In this example, the first graphical display 120 shows the eCO curve 412 over 7 days while the second display 122 shows the data over 3 days. The dashboard view 118 can also include additional information including the latest eCO Burden/Load 124 (or the latest eCO reading from the latest sample), the number of cigarettes 126 over a defined period such as the current day, as well as the amount of nicotine 128. In addition, the dashboard 118 can also include a count of the number of samples 130 provided by the individual over a defined period (such as a daily through monthly count).

The dashboard 118 can also display information that can assist the individual in the reduction or cessation of smoking. For example, FIG. 22 also shows a cost of cigarettes 132 using the count of the portion of cigarettes smoked by the individual 126 or 426. The dashboard can also display social connections 146, 142, 140 to assist in cessation of smoking. For example, the dashboard can display a medical practitioner or counselor 140 that can be directly messaged. In addition, information can be displayed on social acquaintances 142 that are also trying to reduce their own smoking behavior.

The dashboard 118 can also display information regarding smoking triggers 134 as discussed above, for the individual as a reminder to avoid the triggers. The dashboard can also provide the user with additional behavioral information, including but not limited to the results of behavioral questionnaires 136 that the individual previously completed with his/her medical practitioner or counselor.

The dashboard 118 can also selectively display any of the information discussed herein based on an analysis of the individual. For example, it may be possible to characterize the individual's smoking behaviors and associate such behaviors with certain means that are effective in assisting the individual in reducing or ceasing smoking. In these cases, where the individual's behaviors allow for classifying in one or more phenotypes (where the individual's observable traits allow classifying within one or more groups). The dashboard can display information that is found to be effective for that particular phenotype. Furthermore, the information on the dashboard can be selectively adjusted by the user to allow for customization that the individual finds to be effective as a non-smoking motivator.

Figure 23:
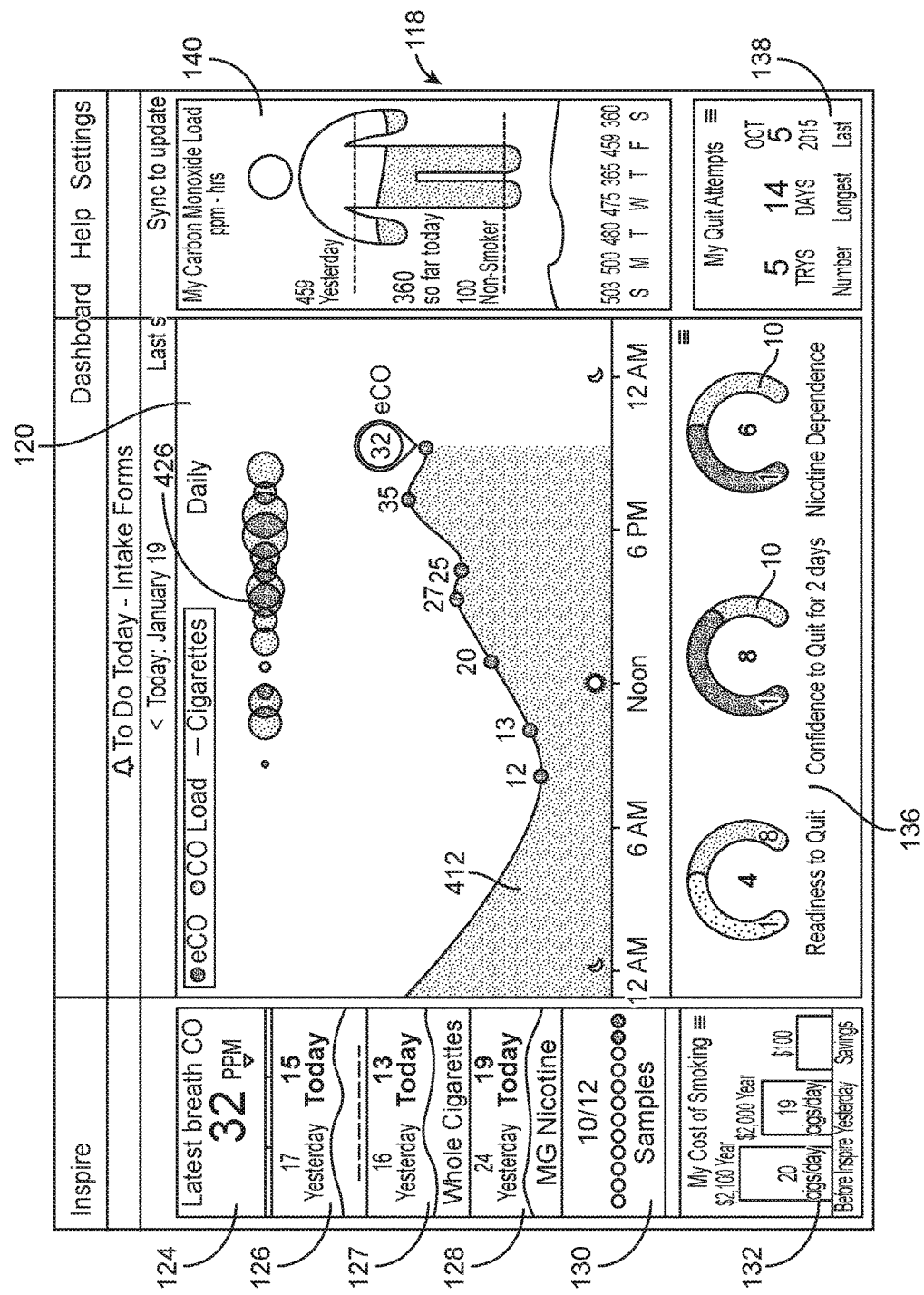
FIG. 23 shows another variation of a dashboard displaying similar information to that shown in FIG. 22.

FIG. 23 shows another variation of a dashboard 118 displaying similar information to that shown in FIG. 22. As noted above, the displayed information is customizable. For example, this variation illustrates the eCO load 140 in a graphical display that shows historical data (yesterday's load), current eCO Burden or load, as well as a target level for that of non-smokers. As shown in FIGS. 22 and 23, the individual previous attempts at quitting smoking 138 can be displayed. In addition, the graphical representation 120 of the eCO trend 412 can be illustrated with individual eCO readings (of the respective sample) can be displayed with information regarding the smoking times 426 as well as a graphic showing the time or duration of smoking (as shown by the circles of varying diameter). As noted above, such information can be entered by the portable sampling unit and displayed in additional forms as shown in 126 and 127, which respectively show historical and current data regarding the number of times smoked and the number of whole cigarettes smoked.

Figure 24A:
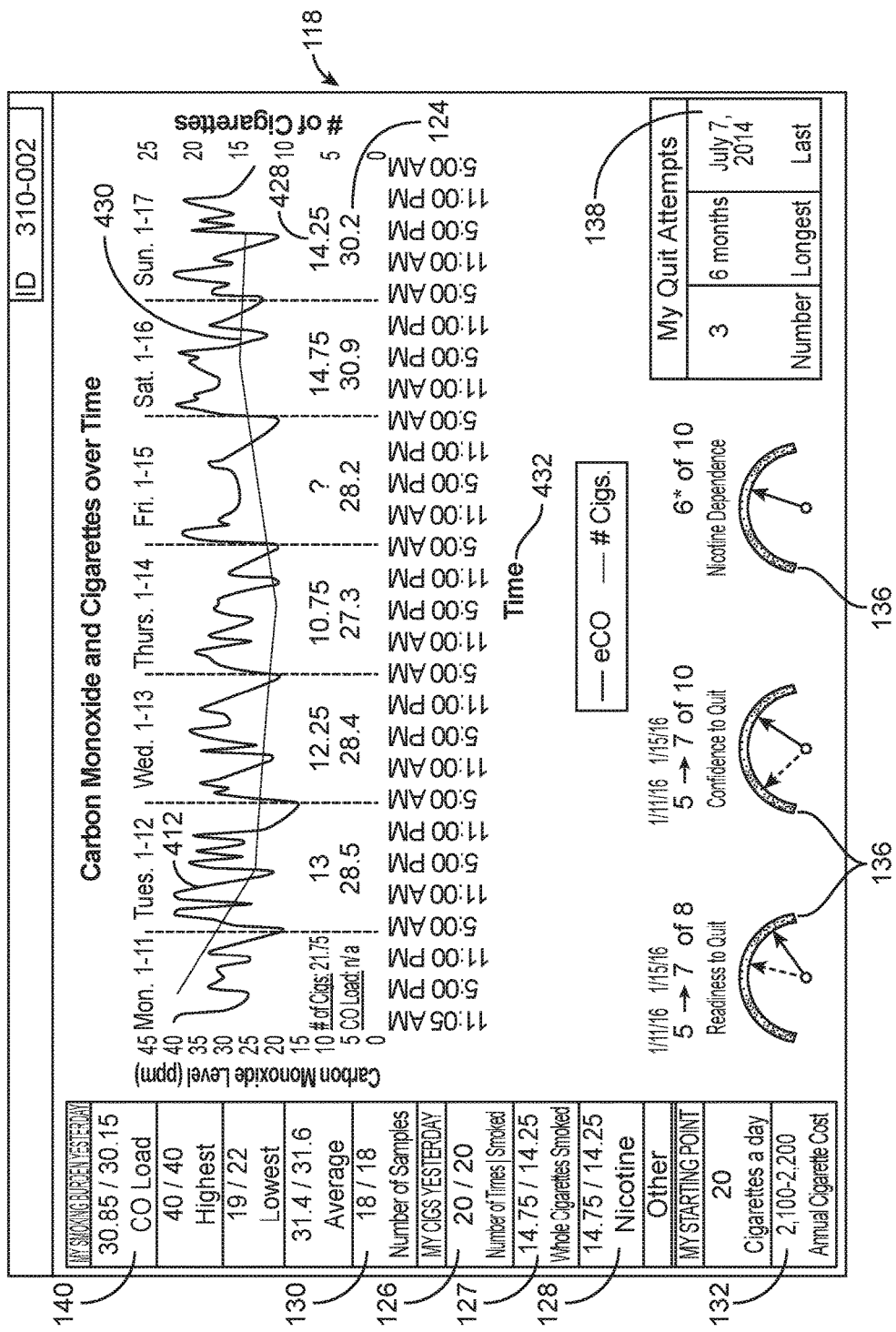
FIGS. 24A to 24C illustrate another variation of a dataset comprising exhaled carbon monoxide, collection time, and cigarette data quantified and displayed to benefit the individual attempting to understand their smoking behavior
Figure 24B:
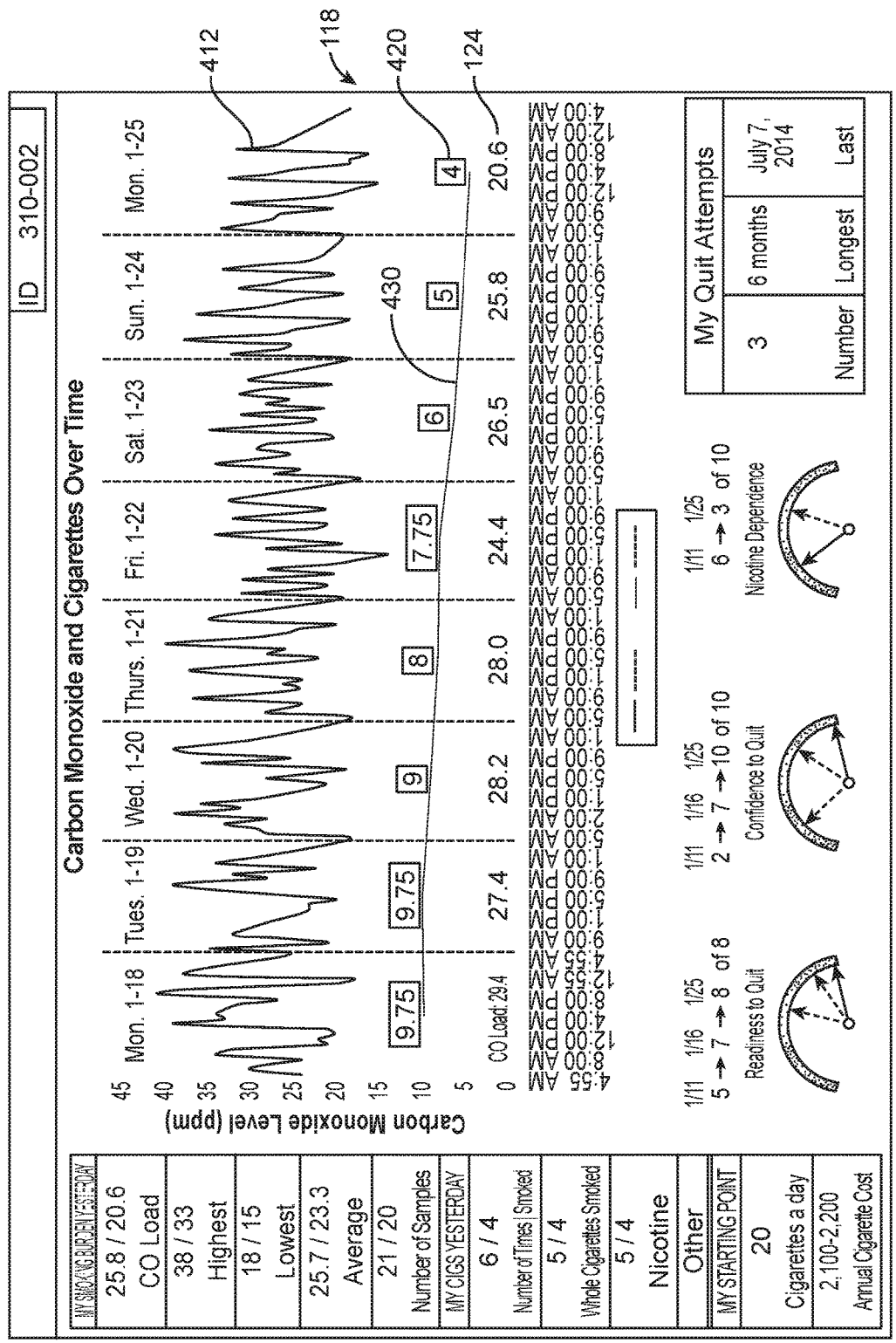
Figure 24C:
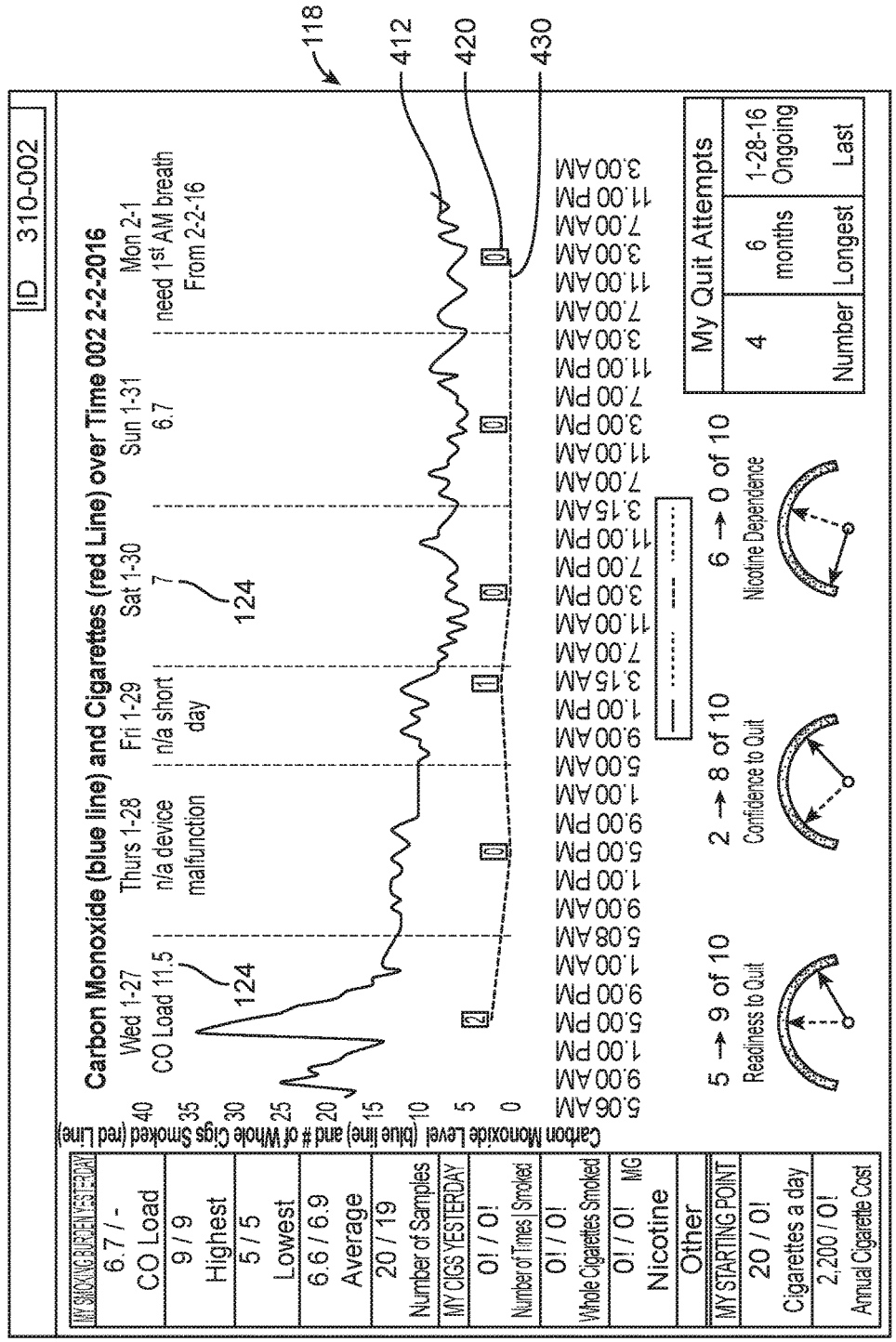

FIGS. 24A to 24C illustrate another variation of a dataset comprising exhaled carbon monoxide, collection time, and cigarette data quantified and displayed to benefit the individual attempting to understand their smoking behavior. FIG. 24A illustrates an example where a patient collected breath samples over the course of a number of days. The example data shown in FIGS. 24A to 24C demonstrate data shown over 21 days but any time range is within the scope of the systems and methods described herein.

As illustrated in FIG. 24A, the period of time 432 is illustrated along the horizontal axis with the time intervals being each day within the time period. Although not shown, during the early stages of sample collection, the time period itself can comprise one or more days with the time interval being a multiple of hours or minutes. Clearly, the longer the time period the greater the ability of the program to select meaningful time intervals within the time period.

FIG. 24A illustrates a variation of a dashboard 118 where smoking data (comprising the total number of cigarettes 428 and an associated curve 430) are superimposed on a graph showing an eCO curve 412. As noted above, the individual provides breath samples on a regular or random basis. In certain variations, the portable sampling unit (not show) prompts the individual to provide samples for measurement of CO. The portable sampling unit allows the samples to be associated with a time stamp and transmits other user generated data as discussed above. The CO data is then quantified to provide a value for the exposure of CO (eCO for exhaled CO) over an interval of time (e.g., per day as shown in FIG. 24A).

FIG. 24A also demonstrates the ability to show historical data simultaneously with present data. For example, the CO load data 140 illustrates the previous day's CO load as well as the highest CO reading, lowest CO reading, and average CO reading. Similar historical is shown regarding the cigarette data as well as the smoking cessation questionnaire results 136.

FIGS. 24B and 24C illustrate the dataset in graphical form as the individual decreases his/her smoking behavior. AS shown in FIG. 24C, as the individual continues to provide samples for measurement of CO, the graphical representation of the dataset shows the individual's self-reporting of smoking fewer cigarettes, which is verified through the reduced values of the CO load 124.

The systems and methods described herein, namely quantification and display of smoking behavior as well as other behavioral data provide a base for which healthcare professionals can leverage into effective programs designed to reduce the effects of cigarette smoke. For example, the system and methods described herein can be used to simply identify a population of smokers from within a general population. Once this population is identified, building the dataset on the individuals specific smoking behavior can be performed prior to attempting to enroll that individual in a smoking cessation program. As noted above, the quantification of the smoking burden (or CO burden) along with the time data of the smoking activity can be combined with other behavioral data to identify smoking triggers unique to that individual. Accordingly, the individual's smoking behavior can be well understood by the healthcare professional prior to selecting a smoking cessation program. In addition, the systems and methods described herein are easily adapted to monitor an individual's behavior once that individual enters a smoking cessation program and can monitor the individual, once they stop smoking, to ensure that the smoking cessation program remains effective and that the individual refrains from smoking.

In addition, the systems and methods described above regarding quantification of smoking behavior can be used to build, update and improve the model for smoking behavior discussed above as well as to provide perturbations to assist in ultimately reducing the individual's smoking behavior.

A number of embodiments of the invention have been described. Nevertheless, it will be understood that various modifications may be made without departing from the spirit and scope of the invention. Combination of the aspect of the variations discussed above as well combinations of the variations themselves are intended to be within the scope of this disclosure.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

What is claimed is:

1. A method of quantifying an individual's smoking behavior, the method comprising:
obtaining a plurality of samples of exhaled air from the individual over a period of time and recording a collection time associated with each sample of exhaled air;
measuring an amount of exhaled carbon monoxide for each of the samples of exhaled air;
compiling a dataset comprising the amount of exhaled carbon monoxide and the collection time for at least two samples of the plurality of samples of exhaled air;
quantifying an additive exposure of exhaled carbon monoxide over an entirety of an interval of time within the period of time and assigning an exhaled carbon monoxide load to the interval of time using the dataset; and
displaying the exhaled carbon monoxide load.

2. The method of claim 1, where obtaining the plurality of samples of exhaled air from the individual over the period of time and recording the collection tune of each sample of exhaled air comprises sequentially obtaining the plurality of samples of exhaled air.

3. The method of claim 1, where quantifying the cumulative exposure of exhaled carbon monoxide comprises correlating a function of exhaled carbon monoxide versus time over the period of time using the dataset.

4. The method of claim 3 further comprising obtaining an area of exhaled carbon monoxide and time under a curve defined by the function over the interval of time.

5. The method of claim 1, further comprising generating a signal to the individual to provide at least one sample of exhaled air.

6. The method of claim 1, further comprising alerting the individual on a repeating basis to provide the sample of exhaled air over the period of time.

7. The method of claim 1, further comprising receiving an input data from the individual and recording a time of the input.

8. The method of claim 7, where the input data comprises at least a count of a portion of a cigarette smoked by the individual.

9. The method of claim 8, further comprising visually displaying a summation of the count of portion of the cigarettes smoked by the individual.

10. The method of claim 8, further comprising determining a cigarette cost using the count of the portion of cigarettes smoked by the individual and displaying the cigarette cost.

11. The method of claim 8, further comprising determining a nicotine estimate using the count of the portion of cigarettes smoked by the individual and displaying the nicotine estimate.

12. The method of claim 7, where the input data comprises a behavioral information of the individual.

13. The method of claim 1, further comprising providing the visual display of the exhaled carbon monoxide load in association with a visual-display interval of time within the period of time.

14. The method of claim 1, further comprising providing a visual display of a count of a number of the plurality of samples of exhaled air.

15. The method of claim 1, further comprising determining a series of exhaled carbon monoxide loads for a series of intervals of time within the period of time.

16. The method of claim 15, further comprising displaying the series of exhaled carbon monoxide loads for the series of intervals of time.

17. The method of claim 1, where measuring the amount of exhaled carbon monoxide comprises using a portable sensor.

18. The method of claim 17, further comprising transmitting the amount of exhaled carbon monoxide and the collection time associated with each sample of exhaled air from the portable sensor to an electronic device.

19. The method of claim 1, further comprising obtaining a location of the individual when obtaining at least one of the plurality of samples of exhaled air.

20. The method of claim 1, further comprising obtaining a result of a behavioral questionnaire from the individual and displaying the result of the behavioral questionnaire with the exhaled carbon monoxide load.

21. The method of claim 1, where quantifying the cumulative exposure of exhaled carbon monoxide over the interval of time within the period of time includes estimating a rate of decay of carbon monoxide.

22. The method of claim 1, where quantifying the cumulative exposure of exhaled carbon monoxide over the interval of time within the period of time includes estimating an increase in a rate of carbon monoxide in the event the individual smokes a cigarette.

23. The method of claim 1, where obtaining the plurality of samples over the period of time comprises engaging the patient to reduce smoking only after the period of time expires such that the first period of time represents the individual's smoking behavior.

24. The method of claim 1, further comprising engaging the patient to reduce smoking only after the first period of time expires.

25. A method of quantifying an individual's smoking behavior, the method comprising:

building a model of the individual's smoking behavior by obtaining a plurality of samples of carbon monoxide from the individual over a period of time and recording a collection time associated with each sample of carbon monoxide;

compiling a dataset comprising the amount of carbon monoxide and the collection time for at least two samples of the plurality of samples of carbon monoxide;

quantifying an additive exposure of carbon monoxide over an entirety of an interval of time within the period of time and assigning a carbon monoxide load to the interval of time using the dataset; and displaying the carbon monoxide load.

26. The method of claim 25, Where obtaining the plurality of samples of carbon monoxide comprises obtaining a plurality of samples of exhaled air from the individual over time and measuring an amount of exhaled carbon monoxide for each of the samples of exhaled air and where recording the collection time associated with each sample of carbon monoxide comprises recording the collection time associated with each sample of exhaled air.

27. The method of claim 25, further comprising delivering a perturbation to the individual.

* * * * *

UNITED STATES PATENT AND TRADEMARK OFFICE
CERTIFICATE OF CORRECTION

PATENT NO. : 9,861,126 B2
APPLICATION NO. : 15/258921
DATED : January 9, 2018
INVENTOR(S) : David S. Utley et al.

It is certified that error appears in the above-identified patent and that said Letters Patent is hereby corrected as shown below:

In the Claims

In Claim 2, Column 38, Line 39, please replace "tune" with --time--.
In Claim 13, Column 39, Line 9, please replace "visual-display" with --visual display--.
In Claim 26, Column 40, Line 29, please replace "Where" with --where--.

Signed and Sealed this
Seventeenth Day of April, 2018

Andrei Iancu
*Director of the United States Patent and Trademark Office*